(12) United States Patent
Zoldan et al.

(10) Patent No.: US 12,054,862 B2
(45) Date of Patent: *Aug. 6, 2024

(54) ELECTROSPUN PNIPAAm/PCL FIBER MATS FOR ALIGNED CELL SHEETS

(71) Applicant: Board of Regents, The University of Texas System, Austin, TX (US)

(72) Inventors: Janeta Zoldan, Austin, TX (US); Alicia Allen, Austin, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 263 days.

This patent is subject to a terminal disclaimer.

(21) Appl. No.: 17/392,805

(22) Filed: Aug. 3, 2021

(65) Prior Publication Data

US 2021/0363675 A1    Nov. 25, 2021

Related U.S. Application Data

(63) Continuation of application No. 16/023,147, filed on Jun. 29, 2018, now Pat. No. 11,111,611.

(60) Provisional application No. 62/528,020, filed on Jun. 30, 2017.

(51) Int. Cl.
| | |
|---|---|
| *D04H 1/728* | (2012.01) |
| *C12N 5/00* | (2006.01) |
| *C12N 5/077* | (2010.01) |
| *C12N 5/079* | (2010.01) |
| *D04H 1/43* | (2012.01) |
| *D04H 1/4334* | (2012.01) |
| *D04H 1/4382* | (2012.01) |
| *D04H 13/00* | (2006.01) |

(52) U.S. Cl.
CPC ......... *D04H 1/4334* (2013.01); *C12N 5/0068* (2013.01); *C12N 5/0618* (2013.01); *C12N 5/0654* (2013.01); *C12N 5/0655* (2013.01); *C12N 5/0657* (2013.01); *C12N 5/0658* (2013.01); *D04H 1/43* (2013.01); *D04H 1/43828* (2020.05); *D04H 1/43835* (2020.05); *D04H 1/43838* (2020.05); *D04H 1/728* (2013.01); *C12N 2533/30* (2013.01); *C12N 2539/10* (2013.01); *D04H 13/002* (2013.01)

(58) Field of Classification Search
None
See application file for complete search history.

(56) References Cited

U.S. PATENT DOCUMENTS

| | | |
|---|---|---|
| 2004/0009566 A1 | 1/2004 | Okano |
| 2009/0317852 A1 | 12/2009 | Parker |
| 2012/0156781 A1 | 6/2012 | Takahashi |
| 2015/0125952 A1* | 5/2015 | Kim ................. A61L 27/3873 |
| | | 435/396 |

FOREIGN PATENT DOCUMENTS

KR    101072476 B1    10/2011

OTHER PUBLICATIONS

Shi et al (Nanoscale, 2016, 8, 2022-2029) (Year: 2016).*
De Oliveira et al (Soft Matter, 2015, 11, 8599) (Year: 2015).*
Akiyama et al., 2004, "Ultratin Poly(N-isopropylacrylamide) Grafted Layer on Polystyrene Surfaces for Cell Adhesion/Detachment Control." Langmuir, 20:5506-5511.
Anderson et al., 1996, "Host Reactions to Biomaterials and their Evaluation." Biomaterials Science: an Introduction to Materials in Medicine, Host reactions to biomaterials and their evaluation, Academic Press, 13 pages.
Beattie et al., 2014, "In situ particle film ATR FTIR spectroscopy of poly (N-isopropyl acrylamide) (PNIPAM) adsorption onto talc." Phys. Chem. Chem. Phys., 16:25143-25151.
Bordes et al., 2010, "Determination of poly(e-caprolactone) solubility parameters: Application to solvent substituion in a microencapsulation process." Int. J. Pharm., 383:236-243.
Chen, M., Dong, M., Havelund, R., Regina, V.R., Meyer, R.L., Besenbacher, F., and Kingshott, P. (2010). Thermo-Responsive Core-Sheath Electrospun Nanofibers from Poly (N-isopropylacrylamide)/Polycaprolactone Blends. Chem. Mater. 22, 4214-4221.
Doshi et al., 1993, "Electrospinning Process and Applications of Electrospun Fibers." Conference Record of the 1993 IEEE Industry Applications Society Annual Meeting, 3:1698-1703.
Dybal et al., 2009, "The role of water in structural changes of poly(N-isopropylacrylamide) an poly(N-isopropylmethacrylamide) studied by FTIR, Raman spectroscopy and quantum chemical calculations." Vib. Spectrosc., 51:44-51.
Elzein et al., 2004, "FTIR study of polycaprolactone chain organization at interfaces." J. Colloid Interface Sci., 273:381-387.
Falconnet et al., 2006, "Surface engineering approaches to micropattern surfaces for cell-based assays." Biomaterials, 27:3044-3063.
Ferdman et al., 1993, "Scattering of Light from Histologic Sections: A New Method for the Analysis of Connective Tissue." J. Invest. Dermatol., 100:710-716.
Haraguchi et al., 2012, "Fabrication of functional three-dimensional tissues by stacking cell sheets in vitro." Nat. Protoc., 7:850-858.
Haraguchi, Y., Shimizu, T., Yamato, M., Kikuchi, A., and Okano, T. (2006). Electrical coupling of cardiomyocyte sheets occurs rapidly via functional gap junction formation. Biomaterials 27, 4765-4774.
Kai et al., 2014, "Stem cell-loaded nanofibrous patch promotes the regeneration of infarcted myocardium with functional improvement in rat model." Acta Biomater., 10:2727-2738.

(Continued)

*Primary Examiner* — Celeste A Roney
(74) *Attorney, Agent, or Firm* — Riverside Law LLP

(57) ABSTRACT

The present invention provides compositions comprising aligned fibers of electrospun PNIPAAm and poly (ε-caprolactone) (PCL) (denoted PNIPAAm/PCL fibers). The PNIPAAm/PCL compositions enable enhanced growth and detachment of intact anisotropic cell sheets. The compositions do not require chemical modification or resource-intensive techniques, thus saving time and expense, and have the potential to generate tissue-specific, aligned cell sheets for transplant studies.

12 Claims, 18 Drawing Sheets

(56) References Cited

OTHER PUBLICATIONS

Kim et al., 2012, "Matrix nanotopography as a regulaor of cell function." J. Cell Biol., 197:351-360.
Lee et al., 2016, "Development of 3D microvascular networks within gelatin hydrogels using thermoresponsive sacrificial microfibers." Adv. Healthcare Mater., 5:781-785.
Lee S et al., "Contractile force generation by 3D hiPSC-derived cardiac tissues is enhanced by rapid establishment of cellular interconnection in matrix with muscle-mimicking stiffness." Biomaterials, 2017, 131:111-120.
Levorson et al., 2013, "Fabrication and characterization of multiscale electrospun scaffolds for cartilage regneration." Biomed. Mater., 8:014103, 12 pages.
Lim et al., 2010, "The effect of nanofiber-guided cell alignment on the preferential differentiation of neural stem cells." Biomaterials, 31:9031-9039.
Moran et al., 2007, "Cell growth and detachment from protein-coated PNIPAAm-based copolymers." J. Biomed. Mater. Res., 81A:870-876.
Moran et al., 2007, "Intact endothelial cell sheet harvesting from thermoresponsive surfaces coated with cell adhesion promoters." J. R. Soc., Interface, 4:1151-1157.
Nam et al., 2008, "Materials Selection and Residual Solvent Retention in Biodegradable Electrospun Fibers." J. Appl. Polym. Sci., 107:1547-1554.
Pelton, 2010, "Poly(N-isopropylacrylamide) (PNIPAM) is never hydrophobic." J. Colloid Interface Sci., 348:673-674.
Pham et al., 2006, "Electrospinning of Polymeric Nanofibers for Tissue Engineering Applications: A Review" Tissue Eng., 12:1197-1211.
Püspöki et al., 2016, "Transforms and Operators for Directional Bioimage Analysis: A Survey." Adv. Anat., Embryol. Cell Biol., 219:69-93.
Rezakhaniha et al., 2012, "Experimental investigation of collagen waviness and orientation in the arterial adventitia using confocal laser scanning microscopy." Biomech. Model. Mechanobiol., 11:461-473.
Rockwood et al., 2008, "Characterization of electrospun poly(N-isopropyl acrylamide) fibers" Polymer, 49:4025-4032.
Shimizu et al., 2002, "Fabrication of Pulsatile Cardiac Tissue Grafts Using a Novel 3-Dimensional Cell Sheet Manipulation Technique and Temperature-Responsive Cell Culture Surfaces." Circ. Res., 90:e40, 9 pages.
Takahashi et al., 2011, "Anisotropic cell sheets for constructing three-dimensional tissue with well-organized cell orientation." Biomaterials, 32:8830-8838.
Takahashi et al., 2011, "Micropatterned Thermoresponsive Polymer Brush Surfaces for Fabricating Cell Sheets with Well-Controlled Orientational Structures." Biomacromolecules, 12:1414-1418.
Thompson et al., 2007, "Effects of parameters on nanofiber diameter determined from electrospinning model." Polymer, 48:6913-6922.
Wang et al., 2009, "Cell adhesion and accelerated detachment on the surface of temperature-sensitive chitosan and poly(N-isopropylacrylamide) hydrogels." J. Mater. Sci.: Mater. Med., 20:583-590.
Wang et al., 2012, "Promoting engraftment of transplanted neural stem cells/progenitors using biofunctionalised electrospun scaffolds." Biomaterials, 33:9188-9197.
Yamada, N., Okano, T., Sakai, H., Karikusa, F., Sawasaki, Y., and Sakurai, Y. (1990). Thermo-responsive polymeric surfaces; control of attachment and detachment of cultured cells. Makromol. Chem., Rapid Commun. 11, 571-576.
Yamato et al., 2007, "Temperature-responsive cell culture surfaces for regenerative medicine with cell sheet engineering." Prog. Polym. Sci., 32:1123-1133.
Yang et al., 2005, "Cell sheet engineering: Recreating tissues without biodegradable scaffolds." Biomaterials, 26:6415-6422.
Yang et al., 2007, "Reconstruction of functional tissues with cell sheet engineering." Biomaterials, 28:5033-5043.
Zhao et al., 2016, "Fabrication of Thermoresponsive Nanofibers for Cell Sorting and Aligned Cell Sheet Engineering." J. Nanosci. Nanotechnol., 16:5520-5527.

* cited by examiner p < 0.05, compared to 0% PNIPAAm fibers

&$p<0.05$ compared to 100% PNIPAAm fibers
*$p < 0.05$, compared all other conditions

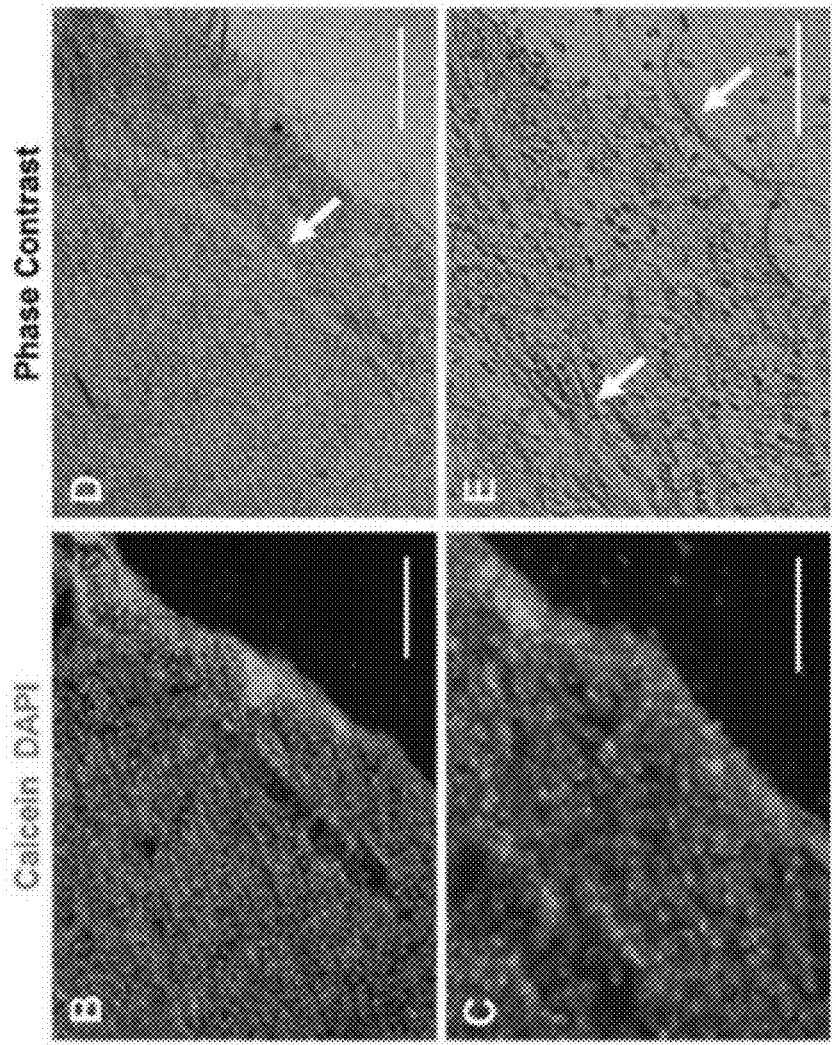
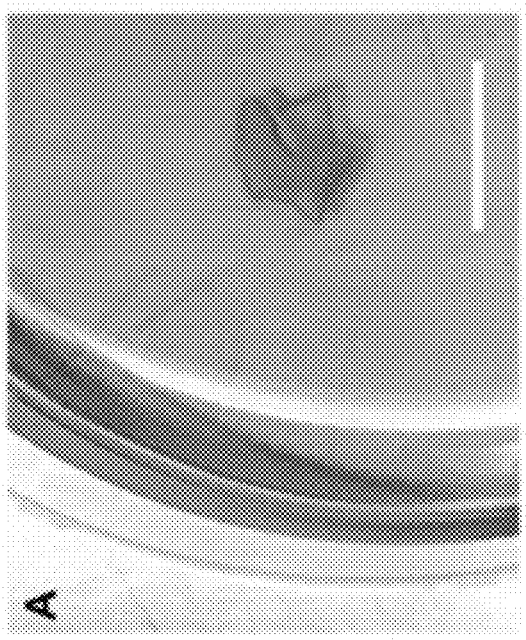

| Position (cm$^{-1}$) | Polymer | Assignment |
|---|---|---|
| 1727 | PCL | Carbonyl stretching |
| 1626 | PNIPAAm | Amide I |
| 1559 | PNIPAAm | Amide II |
| 1462 | PNIPAAm | CH3 asymmetrical deformation |
| 1390, 1371 | PNIPAAm | CH3 symmetrical deformation |
| 1293 | PCL | C-C, C-O stretching |
| 1240 | PCL | C-O-C asymmetric stretching |
| 1190 | PCL | OC-O stretching |
| 1170 | PCL | OOC symmetric stretching |
| 1157 | PCL | C-O, C-C stretching |

Figure 7

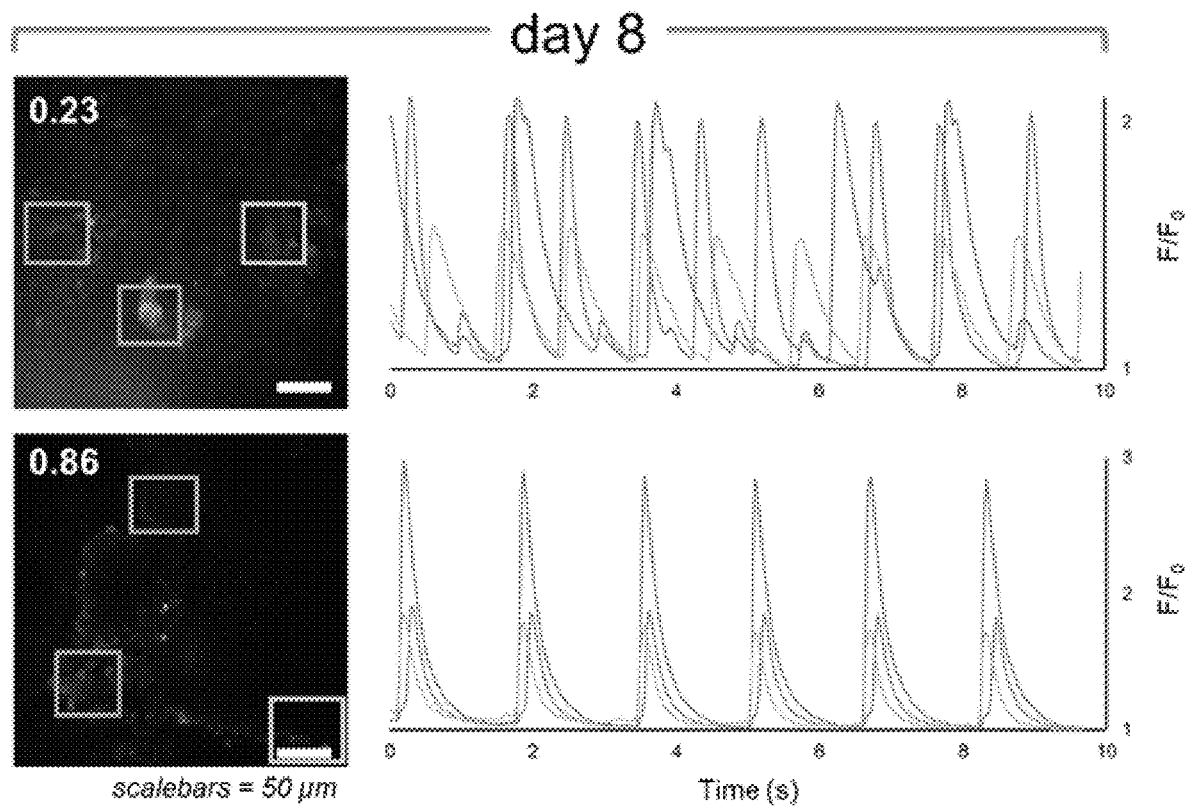
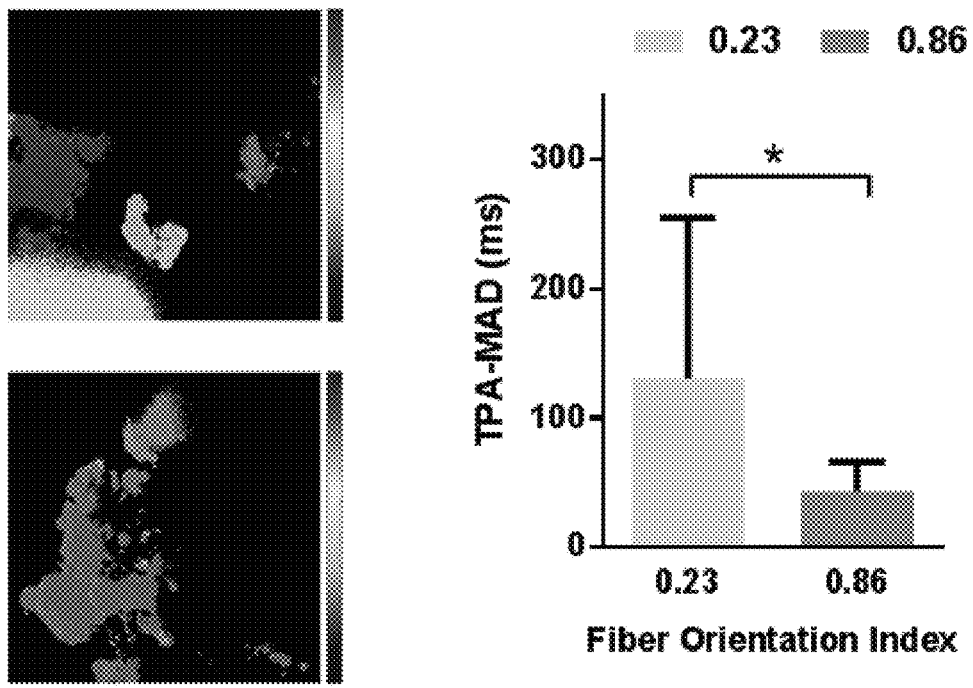
Figure 15

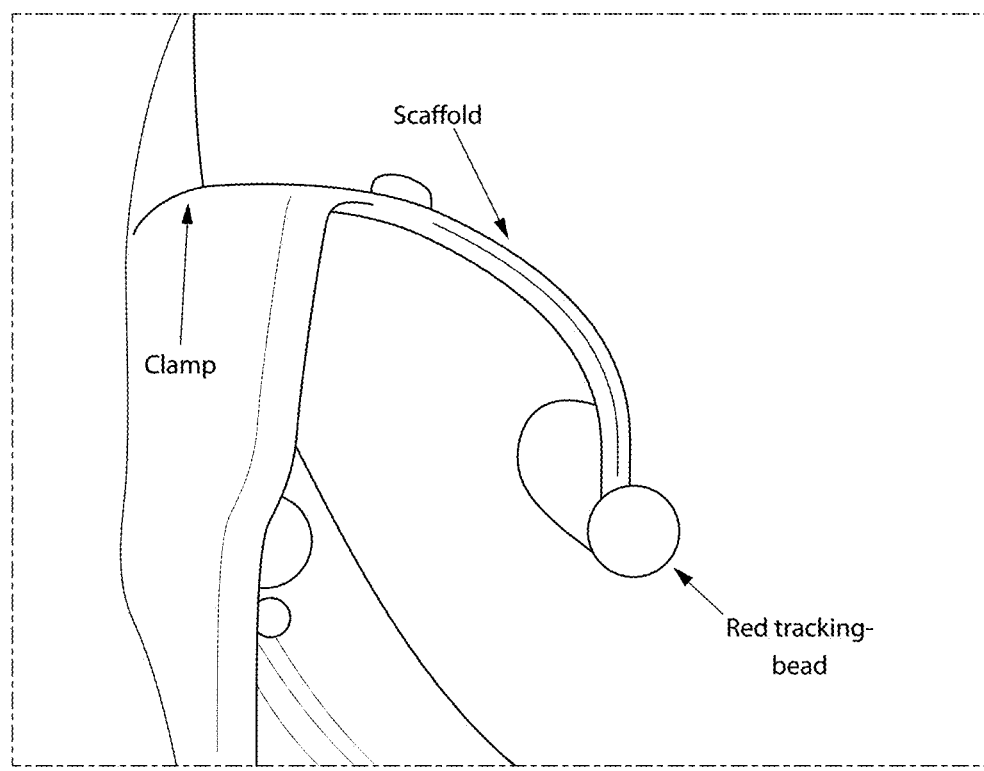
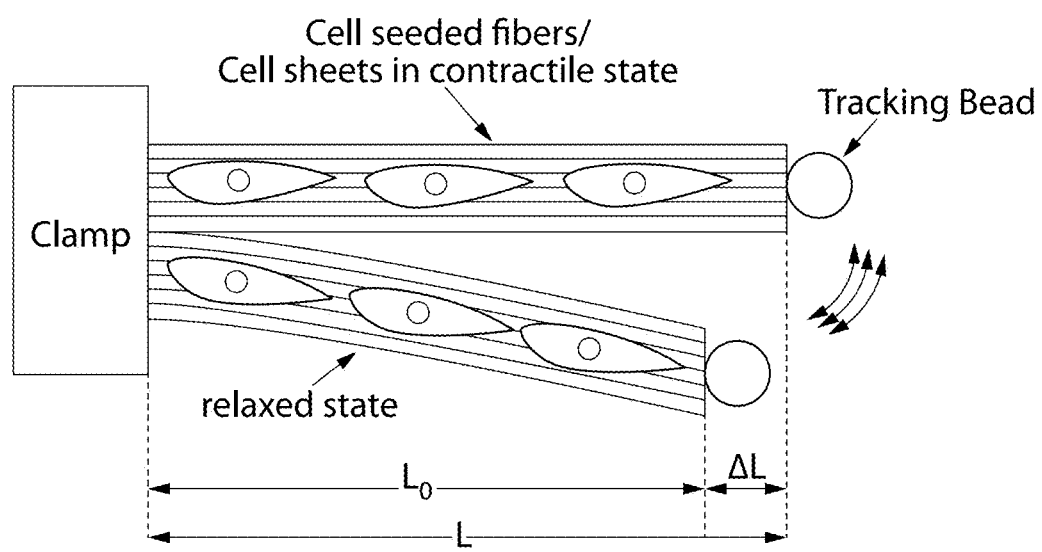
Figure 17

ELECTROSPUN PNIPAAm/PCL FIBER MATS FOR ALIGNED CELL SHEETS

CROSS REFERENCE TO RELATED APPLICATIONS

This application is a continuation of U.S. patent application Ser. No. 16/023,147, filed Jun. 29, 2018, which claims priority to U.S. Provisional Application No. 62/528,020, filed Jun. 30, 2017, each of which is hereby incorporated by reference herein in its entirety.

BACKGROUND OF THE INVENTION

Cell alignment, which can influence developmental and physiological processes, is driven by biophysical cues, particularly matrix nanotopography (Kim et al., 2012, J. Cell Biol., 197:351-360). To better mimic native cell microenvironments in vitro, techniques to generate surface anisotropy, from electrospinning fibers (Lim et al., 2010, Biomaterials, 31:9031-9039; Levorson et al., 2013, Biomed. Mater., 8:014103) to micropatterning to photolithography, have been widely developed and applied to anisotropic tissues, particularly muscle and nervous tissue. Both micropatterning and photolithography can be used to design surfaces with high resolution but are resource-intensive, requiring microprinters and clean rooms (Falconnet et al., 2006, Biomaterials, 27:3044-3063). Electrospinning, on the other hand, is a relatively simple and inexpensive technique to fabricate polymer nano- and micro-fibers that can be seeded with cells (Doshi et al., 1993, Conference Record of the 1993 IEEE Industry Applications Society Annual Meeting, 3:1698-1703; Pham et al., 2006, Tissue Eng., 12:1197-1211). Electrospun fibers are extracellular matrix-mimicking in that they provide a 3-dimensional fibrous microenvironment. Aligned electrospun fibers have been successful as scaffolds for generating nervous and beating cardiac tissues that can be implanted into animal models (Kai et al., 2014, Acta Biomater., 10:2727-2738; Wang et al., 2012, Biomaterials, 33:9188-9197). These transplants, however, are rather limited in that they are only 1-2 cell layers thick, which can severely limit function depending on tissue type, and the material component may elicit a host response upon implantation (Anderson et al., 1996, Biomaterials Science: an Introduction to Materials in Medicine, Host reactions to biomaterials and their evaluation, Academic Press).

Cell sheeting is a technique to generate biomaterial-free, tissue-like constructs for transplant. Teruo Okano pioneered the re-purposing of thermosensitive poly(N-isopropylacrylamide) (PNIPAAm) as a surface coating to enable cell sheeting in vitro (Yamada et al., 1990, Makromol. Chem., Rapid Commun., 11:571-576). PNIPAAm undergoes a rapid coil-to-globule transition at its lower critical solution temperature (LCST) of 32° C. that determines how the hydrophilic and hydrophobic domains interact with water. Below 32° C., PNIPAAm readily dissolves in water; above 32° C., PNIPAAm's hydrophilic domains are sequestered and PNIPAAm precipitates in aqueous solutions (Pelton, 2010, J. Colloid Interface Sci., 348:673-674). Thus, for cells grown on PNIPAAm-grafted tissue culture plates, cell sheet detachment is possible when the incubation temperature is lowered below the LCST: PNIPAAm expands, forcing the cell sheet to detach without perturbing cell-cell and cell-ECM adhesions. Using this technique, cells sheets have been generated for transplantation to the heart, cornea, and kidney (Yang et al., 2005, Biomaterials, 26:6415-6422, Yamato et al., 2007, Prog. Polym. Sci., 32:1123-1133). Yet generating aligned cell sheets has been challenging. Although grafting hydrophilic domains to PNIPAAm-grafted plates spatially controls cell attachment, leading to cell alignment, this approach required chemical synthesis and photolithography patterning (Takahashi et al., 2011, Biomaterials, 32:8830-8838; Takahashi et al., 2011, Biomacromolecules, 12:1414-1418).

Thus, there is a need in the art for improved materials and methods for generating aligned cell sheets for various applications, including tissue graft therapy. The present invention addresses this unmet need.

SUMMARY OF THE INVENTION

In one aspect, the present invention relates to a fiber mat comprising poly(N-isopropylacrylamide) (PNIPAAm) and poly(caprolactone) (PCL), wherein the ratio of PNIPAAm to PCL is between 50% (1:1 PNIPAAm:PCL) to 99% (99:1 PNIPAAm:PCL).

In one embodiment, the ratio of PNIPAAm to PCL is 90% (9:1 PNIPAAm:PCL). In one embodiment, the ratio of PNIPAAm to PCL is 75% (3:1 PNIPAAm:PCL). In one embodiment, the fiber mat has fibers with a diameter between about 1 and 3 μm. In one embodiment, the fiber mat has fibers formed from a PNIPAAm core and a PCL shell. In one embodiment, the fiber mat has PNIPAAm fibers and PCL fibers. In one embodiment, the fiber mat has fibers arranged substantially in parallel.

In another aspect, the present invention relates to a method of making an anisotropic cell sheet, comprising the steps of: electrospinning a solution comprising poly(N-isopropylacrylamide) (PNIPAAm) and poly(caprolactone) (PCL) to generate a fiber mat having fibers in substantially parallel alignment; culturing cells on the fiber mat in an environment above about 32° C. to form an anisotropic sheet of cells attached to the fiber mat; and introducing the fiber mat to an aqueous environment below about 32° C. to release an intact anisotropic sheet of cells.

In one embodiment, the solution comprises a PNIPAAm and PCL mixture having a PNIPAAm to PCL ratio of between 50% (1:1 PNIPAAm:PCL) to 99% (99:1 PNIPAAm:PCL). In one embodiment, the PNIPAAm to PCL ratio is 90% (9:1 PNIPAAm:PCL). In one embodiment, the PNIPAAm to PCL ratio is 75% (3:1 PNIPAAm:PCL). In one embodiment, the solution comprises 10% to 20% wt/v of the PNIPAAm and PCL mixture dissolved in a mixture of methanol and chloroform.

In one embodiment, the electrospinning is performed using a rotating mandrel. In one embodiment, the fibers have a PNIPAAm core and a PCL shell. In one embodiment, the fibers comprise PNIPAAm fibers and PCL fibers. In one embodiment, the fibers have a diameter between about 1 and 3 μm.

In one embodiment, the fiber mat is wetted with an aqueous solution above about 32° C. prior to the step of culturing cells. In one embodiment, the fiber mat is pre-treated with a cell attachment enhancing composition prior to the step of culturing cells. In one embodiment, the attachment enhancing composition comprises at least one component selected from the group consisting of: Matrigel, fetal bovine serum, gelatin, chitosan, fibronectin, collagen, poly-1-lysine, and laminin.

In one embodiment, the cells are selected from the group consisting of: urothelial cells, mesenchymal cells, muscle cells, myocytes, fibroblasts, chondrocytes, adipocytes, fibromyoblasts, ectodermal cells, hepotocytes, Islet cells, parenchymal cells, osteoblasts, nerve cells, and stem cells. In one embodiment, the fiber mat is introduced to an aqueous environment below about 32° C. by immersion or by rinsing.

In another aspect, the present invention relates to an anisotropic cell sheet formed by the method of the present invention.

BRIEF DESCRIPTION OF THE DRAWINGS

The following detailed description of embodiments of the invention will be better understood when read in conjunction with the appended drawings. It should be understood that the invention is not limited to the precise arrangements and instrumentalities of the embodiments shown in the drawings.

(FIG. 1A) Scanning electron microscopy (SEM) images of electrospun PNIPAAm/PCL fibers. Percentage in upper left indicates PNIPAAm content. Scalebars (black bars, bottom left) are 10 μm. (FIG. 1B) Average fiber diameter determined using OrientationJ. (FIG. 1C) Fiber orientation index determined using OrientationJ. *p<0.05 compared to 0% PNIPAAm fibers.

(FIG. 2C) FTIR spectra of PNIPAAm/PCL fibers. Dashed lines indicate absorption peaks.

(FIG. 3A) PNIPAAm/PCL mass loss in water. PNIPAAm/PCL fiber (FIG. 3B) area percent change and (FIG. 3C) axes (relative to fiber direction) length percent change following PNIPAAm dissolution. #p<0.05 compared to all other groups.

(FIG. 4A) Advancing water contact angle on PNIPAAm/PCL fibers. (FIG. 4B) Representative images of water droplet on fibers. White dashed lines indicate fiber edge. *p<0.05 compared to 0% PNIPAAm fibers. & p<0.05 compared to 100% PNIPAAm fibers.

(FIG. 5A) Cell viability relative to 0% PNIPAAm fibers determined by 3-(4,5-dimethylthiazol-2-yl)-5-(3-carboxymethoxyphenyl)-2-(4-sulfophenyl)-2H-tetrazolium (MTS) assay. *p<0.05 compared to 0% PNIPAAm fibers. (FIG. 5B) Representative images of fibroblasts seeded on PNIPAAm/PCL fibers with actin (left) and actin/DAPI overlays (right). Scalebars are 200 μm. (FIG. 5C) Insets from 90% PNIPAAm images, as indicated by white dashed-box in (FIG. 5B). Scalebar is 50 μm. * p<0.05 compared to 0% PNIPAAm fibers.

FIG. 6A through FIG. 6E depict results from example experiments demonstrating cell sheet detachment. (FIG. 6A) Cell sheets detached from 90% PNIPAAm fibers using room temperature medium; scalebar is 1 cm. (FIG. 6B, FIG. 6C) Cell sheet viability was confirmed with calcein, AM live-staining. (FIG. 6D, FIG. 6E) Corresponding phase contrast images of (FIG. 6B, FIG. 6C); white arrows indicate residual PCL. Scalebars are (FIG. 6B, FIG. 6D) 400 μm and (FIG. 6C, FIG. 6E) 200 μm.

FIG. 7 depicts absorption peaks and assignments for PNIPAAm and PCL.

FIG. 15 depicts additional data processing from the results of FIG. 14. The bottom left images are heatmap signals evaluating the beating of the entire culture on the fiber sheet. The top heatmap shows signals originating at different time points in the culture on the fiber sheet having an alignment scale of 0.23. The bottom heatmap shows signals originating at substantially the same time in the culture on the fiber sheet having an alignment scale of 0.86. The bottom right image is a bar graph generated from the quantification of the signal timings in the heatmaps (y-axis label: time for point arrival-median absolute deviation).

FIG. 17 depicts a schematic and actual testing setup of cantilever bending. Cardiomyocyte contraction causes the cantilever to move upwards, and the resulting change in length is recorded. Scale bar=10 mm. Cantilever bending was only detected in cardiomyocytes that were differentiated on aligned fiber scaffolds and were beating synchronously.

DETAILED DESCRIPTION

Figure 1A:
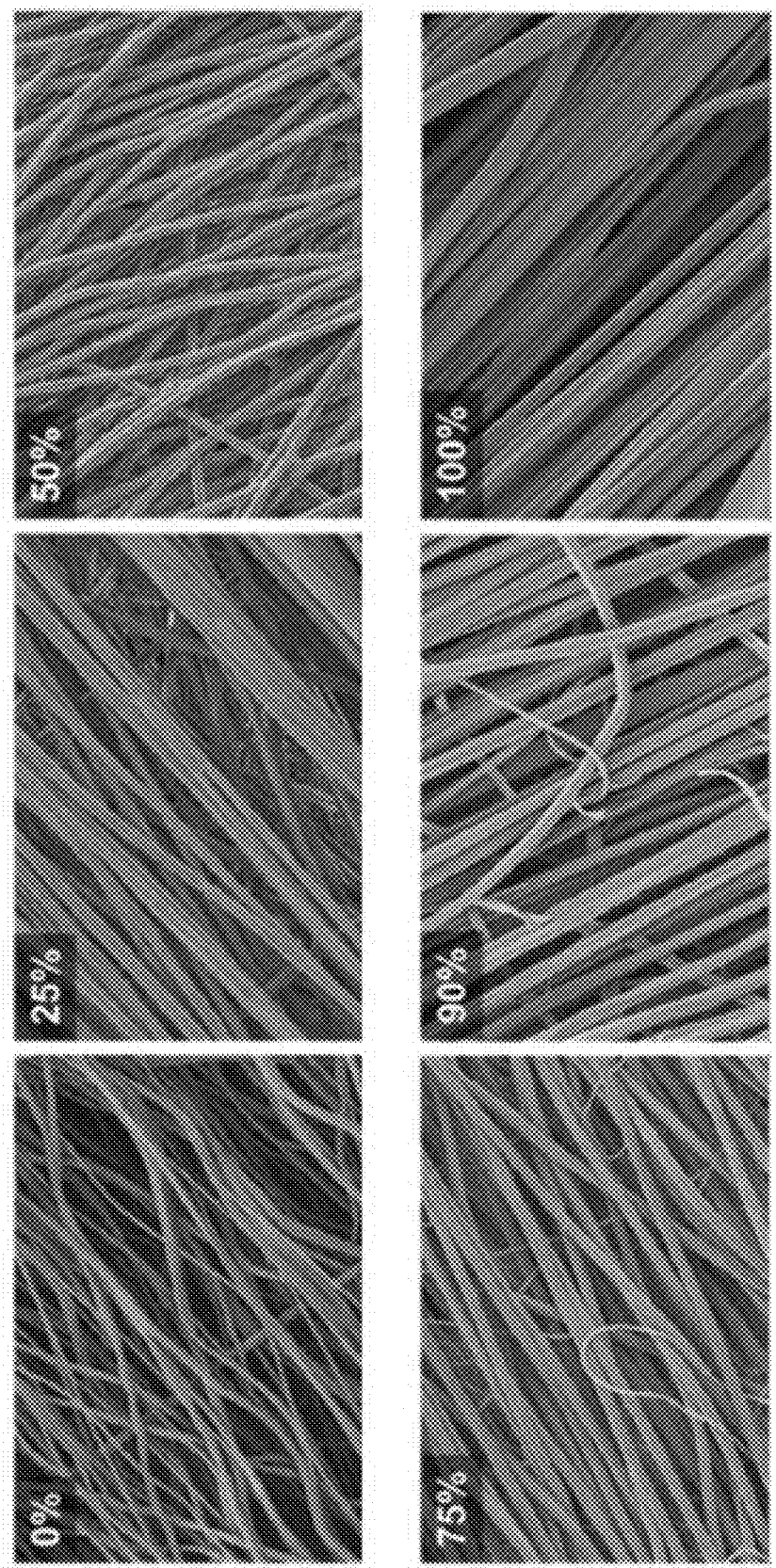
FIG. 1A through FIG. 1C depict results from example experiments demonstrating PNIPAAm/PCL fibers.

The present invention provides compositions comprising aligned fibers of electrospun PNIPAAm and poly (ε-caprolactone) (PCL). The PNIPAAm/PCL compositions enable enhanced growth and detachment of intact anisotropic cell sheets. The compositions demonstrate an unexpected and significant benefit in that they do not require chemical modification or resource-intensive techniques, thus saving time and expense, and have the potential to generate tissue-specific, aligned cell sheets for a wide variety of applications, including but not limited to tissue repair and drug screening.

Definitions

It is to be understood that the figures and descriptions of the present invention have been simplified to illustrate elements that are relevant for a clear understanding of the present invention, while eliminating, for the purpose of clarity, many other elements typically found in the art. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, exemplary methods and materials are described As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

PNIPAAm/PCL Fiber Mats

The present invention relates in part to the unexpected discovery that PNIPAAm and PCL in solution can be electrospun into mats of uniquely structured fibers in substantially parallel alignment. Further, it is described herein that mats formed from electrospun PNIPAAm/PCL at certain ratios are capable of supporting cell cultures forming intact cell sheets. The electrospun mats can include PNIPAAm fibers alongside PCL fibers, and can include fibers having a PNIPAAm core and a PCL sheath.

Electrospinning is a process exploiting the interactions between an electrostatic field and a conducting fluid. When an external electrostatic field is applied to a conducting fluid (e.g., a semi-dilute polymer solution or a polymer melt), a suspended conical droplet is formed, whereby the surface tension of the droplet is in equilibrium with the electric field. As it reaches a grounded target, the material can be collected as an interconnected web containing relatively fine, i.e. small diameter, fibers. The resulting films (or membranes) from these small diameter fibers have very large surface area to volume ratios and small pore sizes.

Electrospinning involves the spinning of non-woven fabric of solutions or melts using very high voltages. The solvent is pumped to a needle, called the spinneret, where a very high voltage is applied. If this voltage is high enough, the repelling charges will be stronger than the surface tension will keep the solution together, and generate a charged jet from the Taylor cone at the needle tip. By placing a differently charged target at a defined distance, these cones will start to deposit very thin fibers onto the target.

The present invention combines the temperature-dependent dissolution aspects of PNIPAAm with cell attachment aspects of PCL to electrospin aligned fiber mats capable of supporting the growth and intact release of anisotropic cell sheets. Accordingly, the present invention provides PNIPAAm and PCL blends for electrospinning. In various embodiments, the blends comprise a PNIPAAm to PCL ratio of between 50% (1:1 PNIPAAm:PCL) and 99% (99:1 PNIPAAm:PCL). In some embodiments, the blends comprise a PNIPAAm to PCL ratio of between 75% (3:1 PNIPAAm:PCL) and 90% (9:1 PNIPAAm:PCL). In various embodiments, the blends comprise a PNIPAAm to PCL ratio of 75%, 76%, 77%, 78%, 79%, 80%, 81%, 82%, 83%, 84%, 85%, 86%, 87%, 88%, 89%, or 90%. The PNIPAAm and PCL can be dissolved in any suitable solvent. Typical solvents include N,N-Dimethyl formamide (DMF), tetrahydrofuran (THF), methylene chloride, methanol, dioxane, ethanol, hexafluoroisopropanol (HFIP), chloroform, glacial acetic acid, water, and combinations thereof. For example, in one embodiment the solvent is a mixture of methanol and chloroform. In one embodiment, the PNIPAAm/PCL blend comprises between 10 and 20% wt/v of a PNIPAAm/PCL composition dissolved in a mixture of methanol and chloroform.

In certain embodiments the mixture of methanol and chloroform having a ratio of about 10:1 to about 1:10 of methanol to chloroform. In one embodiment, the PNIPAAm/PCL is dissolved in a 1:3 mixture of methanol and chloroform.

The PNIPAAm/PCL blends are amenable to modification to enhance fiber generation, fiber structure, cell attachment, cell growth, and the like. For example, in one embodiment, the blends can optionally contain a salt to create an excess charge effect to facilitate the electrospinning process. Examples of suitable salts include NaCl, $KH_2PO_4$, $K_2HPO_4$, $KIO_3$, KCl, $MgSO_4$, $MgCl_2$, $NaHCO_3$, $CaCl_2$ or mixtures of these salts.

In one embodiment, the blends can include biopolymers, such as extracellular matrix proteins, while maintaining the PNIPAAm to PCL ratio. Exemplary biopolymers include but are not limited to collagen, fibrin, elastin, gelatin, fibrinogen, thrombin, laminin, chondroitin sulfates, heparins, hyaluronic acid, alginate, dextran, pectin, and chitosan. In certain embodiments, the biological component comprises amino acids, peptides, proteins, carbohydrates, lipids, nucleic acids, glycoproteins, minerals, lipoproteins, glycolipids, glycoaminoglycans, and proteoglycans.

In various embodiments, the blends can further comprise one or more synthetic material while maintaining the PNIPAAm to PCL ratio. The synthetic materials are preferably biologically compatible to support cell growth. Such polymers include but are not limited to the following: poly (urethanes), poly(siloxanes) or silicones, poly(ethylene), poly(vinyl pyrrolidone), poly(2-hydroxy ethyl methacrylate), poly(N-vinyl pyrrolidone), poly(methyl methacrylate), poly(vinyl alcohol), poly(acrylic acid), poly(ethylene-co-vinyl acetate), poly(ethylene glycol), poly(methacrylic acid), polylactic acid (PLA), polyglycolic acids (PGA), poly(lactide-co-glycolides) (PLGA), nylons, polyamides, polyanhydrides, poly(ethylene-co-vinyl alcohol) (EVOH), poly(vinyl acetate) (PVA), polyvinylhydroxide, poly(ethylene oxide) (PEO) and polyorthoesters or any other similar synthetic polymers that may be developed that are biologically compatible. Polymers with cationic moieties can also be used, such as poly(allyl amine), poly(ethylene imine), poly(lysine), and poly(arginine). The polymers may have any molecular structure including, but not limited to, linear, branched, graft, block, star, comb, and dendrimer structures.

Method of Generating PNIPAAm/PCL Fibers Mats

As described elsewhere herein, the PNIPAAm/PCL blends are electrospun to generate PNIPAAm/PCL fiber mats. The blends are electrospun onto a rotating mandrel to generate mats of blended fibers aligned substantially in parallel. The conditions under which the blends are spun can be performed within any suitable range, such as those disclosed herein. For example, the electric field used in the electrospinning process can be in the range of about 1 to about 50 kV, more preferably from about 5 to about 15 kV. The feed rate of the blend to the spinneret can be in the range of about 1 to about 2 mL/hour. The working distance of the spinneret to the rotating substrate can be in the range of about 5 to about 15 cm, or more preferably about 10 to about 11 cm.

Persons skilled in the art will understand that the rotating substrate typically involves a mandrel mechanically attached to a motor, often through a drill chuck. In various embodiments, the motor rotates the mandrel at a speed of between about 1 revolution per minute (rpm) to about 40,000 rpm. In one exemplary embodiment, the rotation speed is between about 2500 rpm to about 3500 rpm.

The resultant PNIPAAm/PCL fiber mats comprise aligned fibers of between 1 and 3 μm in diameter. As described elsewhere herein, the PNIPAAm core enables temperature-dependent dissolution for controlled release of cultured cells. In some embodiments, fibers comprising a PNIPAAm core are protected by a PCL shell while enhancing cell attachment to the fibers. In other embodiments, PNIPAAm fibers are protected by adjacent PCL fibers. Post-electrospinning, the PNIPAAm/PCL fiber mats can be treated in any suitable manner, such as being cut into any various shapes and sizes, sterilized, and stored for later use.

The PNIPAAm/PCL fiber mats are amenable to modification to enhance cell attachment, cell growth, and the like. In various embodiments, the PNIPAAm/PCL fiber mats can be modified with one or more functional groups for covalently attaching a variety of proteins (e.g., collagen) or compounds such as therapeutic agents. Therapeutic agents which may be linked to the fiber mats include, but are not limited to, analgesics, anesthetics, antifungals, antibiotics, anti-inflammatories, anthelmintics, antidotes, antiemetics, antihistamines, anti-cancer drugs, antihypertensives, antimalarials, antimicrobials, antipsychotics, antipyretics, antiseptics, antiarthritics, antituberculotics, antitussives, antivirals, cardioactive drugs, cathartics, chemotherapeutic agents, a colored or fluorescent imaging agent, corticoids (such as steroids), antidepressants, depressants, diagnostic aids, diuretics, enzymes, expectorants, hormones, hypnotics, minerals, nutritional supplements, parasympathomimetics, potassium supplements, radiation sensitizers, a radioisotope, fluorescent nanoparticles such as nanodiamonds, sedatives, sulfonamides, stimulants, sympathomimetics, tranquilizers, urinary anti-infectives, vasoconstrictors, vasodilators, vitamins, xanthine derivatives, and the like. The therapeutic agent may also be other small organic molecules, naturally isolated entities or their analogs, organometallic agents, chelated metals or metal salts, peptide-based drugs, or peptidic or non-peptidic receptor targeting or binding agents.

In various embodiments, the PNIPAAm/PCL fiber mats can further be modified to comprise one or more polysaccharides, including glycosaminoglycans (GAGs) or glucosaminoglycans, with suitable viscosity, molecular mass, and other desirable properties. The term "glycosaminoglycan" is intended to encompass any glycan (i.e., polysaccharide) comprising an unbranched polysaccharide chain with a repeating disaccharide unit, one of which is always an amino sugar. These compounds as a class carry a high negative charge, are strongly hydrophilic, and are commonly called mucopolysaccharides. This group of polysaccharides includes heparin, heparan sulfate, chondroitin sulfate, dermatan sulfate, keratan sulfate, and hyaluronic acid. These GAGs are predominantly found on cell surfaces and in the extracellular matrix. The term "glucosaminoglycan" is also intended to encompass any glycan (i.e. polysaccharide) containing predominantly monosaccharide derivatives in which an alcoholic hydroxyl group has been replaced by an amino group or other functional group such as sulfate or phosphate. An example of a glucosaminoglycan is poly-N-acetyl glucosaminoglycan, commonly referred to as chitosan. Exemplary polysaccharides that may be useful in the present invention include dextran, heparan, heparin, hyaluronic acid, alginate, agarose, carageenan, amylopectin, amylose, glycogen, starch, cellulose, chitin, chitosan and various sulfated polysaccharides such as heparan sulfate, chondroitin sulfate, dextran sulfate, dermatan sulfate, or keratan sulfate.

In one embodiment, the PNIPAAm/PCL fiber mats can further be modified to comprise one or more natural or synthetic drug, such as nonsteroidal anti-inflammatory drugs (NSAIDs). In one embodiment, the fiber mats can further comprise antibiotics, such as penicillin. In one embodiment, the fiber mats can further comprise natural peptides, such as glycyl-arginyl-glycyl-aspartyl-serine (GRGDS), arginylglycylaspartic acid (RGD), and amelogenin. In one embodiment, the fiber mats can further comprise proteins, such as chitosan and silk. In one embodiment, the fiber mats can further comprise sucrose, fructose, cellulose, or mannitol. In one embodiment, the fiber mats can further comprise extracellular matrix proteins, such as fibronectin, vitronectin, laminin, collagens, and vixapatin (VP12). In one embodiment, the fiber mats can further comprise disintegrins, such as VLO4. In one embodiment, the fiber mats can further comprise decellularized or demineralized tissue. In one embodiment, the fiber mats can further comprise synthetic peptides, such as emdogain. In one embodiment, the fiber mats can further comprise nutrients, such as bovine serum albumin. In one embodiment, the fiber mats can further comprise vitamins, such as vitamin B2, vitamin Ad, Vitamin D, Vitamin E, and Vitamin K. In one embodiment, the fiber mats can further comprise nucleic acids, such as mRNA and DNA. In one embodiment, the fiber mats can further comprise natural or synthetic steroids and hormones, such as dexamethasone, hydrocortisone, estrogens, and its derivatives. In one embodiment, the fiber mats can further comprise growth factors, such as fibroblast growth factor (FGF), transforming growth factor beta (TGF-β), and epidermal growth factor (EGF). In one embodiment, the fiber mats can further comprise a delivery vehicle, such as nanoparticles, microparticles, liposomes, viral and non-viral transfection systems.

Method of Generating Anisotropic Cell Sheets

The PNIPAAm/PCL aligned fiber mats of the present invention enable enhanced anisotropic cell sheet growth and detachment. The fiber mats serve as the substrate for cell attachment and proliferation, and upon incubation or rinsing of the fiber mats with aqueous solution below the critical temperature of 32° C., the PNIPAAm portion of the fibers dissolute, the remaining PCL portion breaks down, and an intact cell sheet is released free of any fibers. In certain embodiments, the PNIPAAm/PCL fiber mats are wetted prior to seeding cells to improve fiber mat handling. Wetting can be accomplished using any suitable liquid media at a temperature above 32° C., such as water, phosphate buffered saline, fetal bovine serum, and any typical cell culture media.

The PNIPAAm/PCL fiber mats are amenable to any suitable cell culture. Typical cell include, but are not limited to: urothelial cells, mesenchymal cells, especially smooth or skeletal muscle cells, myocytes (muscle stem cells), fibroblasts, chondrocytes, adipocytes, fibromyoblasts, and ectodermal cells, including ductile and skin cells, hepotocytes, Islet cells, cells present in the intestine, and other parenchymal cells, osteoblasts and other cells forming bone or cartilage, nerve cells, and stem cells. Stem cells include but are not limited to: embryonic stem cells, fetal stem cells, adult stem cells, induced pluripotent stem cells, mesenchymal stem cells, hematopoietic stem cells, neural stem cells, and epithelial stem cells. Selection of cell types, and seeding of cells onto the fiber mats, will be routine to one of ordinary skill in the art in light of the teachings herein.

The anisotropic cell sheets are able to mimic characteristics of the cell origin tissues. For example, epithelial cells cultured on the fiber mats can form epithelial tissue, liver cells cultured on the fiber mats can form liver tissue, kidney cells cultured on the fiber mats can form kidney tissue, endothelial cells cultured on the fiber mats can form endothelial tissue, skeletal muscle cells cultured on the fiber mats can form skeletal muscle tissue, cardiac muscle cells cultured on the fiber mats can form cardiac muscle tissue, interstitial valvular cells cultured on the fiber mats can form valvular tissue, and the like.

The anisotropic cell sheets can be useful for wound care and tissue regeneration. In one aspect, the anisotropic cell sheets can be used as organ or tissue grafts. The anisotropic cell sheets can be used to treat wounds or tissue damage resulting from trauma, disease, burns, ulcers, abrasions, lacerations, surgery, or other damage. The anisotropic cell sheets can also be used to treat internal soft tissue wounds or defects such as wounds in the amniotic sac, ulcers in the gastrointestinal tract or mucous membranes, gingival damage or recession, damaged or diseased cardiac tissue, damaged or diseased skeletal muscle tissue, internal surgical incisions or biopsies, and the like. Surgeons can use these grafts to cover and protect the area in need of treatment, to temporarily replace lost or damaged tissue, and to guide new tissue generation and healing into the damaged area. The anisotropic cell sheets may be secured to the treatment area using sutures, adhesives, or overlaying bandages. The anisotropic cell sheets may be cut to match the size of the treatment area, or may overlap the edges of the treatment area.

In some embodiments, grafted anisotropic cell sheets are also useful for delivery of biologics, enzymes that activate drugs, protease inhibitors, and the like. The anisotropic cell sheets can include native cells as well as nonnative cells that have the ability to express angiogenic growth factors and cytokines, secrete wound healing related cytokines, secrete collagen, and promote wound healing in vivo. The anisotropic cell sheets may also be embedded or conjugated with various factors which may be released at a graft site. These factors may include, but are not limited to epidermal growth factor (EGF), platelet derived growth factor (PDGF), basic fibroblast growth factor (bFGF), transforming growth factor-β (TGF-β), and tissue inhibitors of metalloproteinases (TIMP), which have been shown to be beneficial in wound healing. Additional healing factors such as antibiotics, bacteriocides, fungicides, silver-containing agents, analgesics, and nitric oxide releasing compounds can also be incorporated into the anisotropic cell sheets.

In some embodiments, the anisotropic cell sheets can be used in cell- or tissue-based screening. In some embodiments, the screening can be for one or more infectious diseases such as viral infection or parasitic infection. In some embodiments, the screening can be for injuries and secondary injuries such as scarring and inflammation. In some embodiments, the screening can be for abnormalities such as atrophy and hypertrophy. In some embodiments, the screening can be for one or more metabolic deficiencies. In some embodiments, the screening can be for one or more protein deficiencies. In some embodiments, the screening can be for cancer, including the study of cancer initiation, progression, or metastasis. In some embodiments, the anisotropic cell sheets can be used in the study of the interaction of other cell types, such as cancer cells, pathogen-bearing cells, pathogenic cells, immune cells, blood-derived cells, or stem/progenitor cells.

In some embodiments, the anisotropic cell sheets can be used for drug screening or drug discovery. In some embodiments, an array, microarray, or chip can incorporate the anisotropic cell sheets for drug screening or drug discovery. In some embodiments, an anisotropic cell sheet can be sectioned and distributed to each well of a biocompatible multi-well container, wherein the container is compatible with one or more automated drug screening procedures and/or devices. The drug screening or drug discovery can be used to research or develop drugs potentially useful in any therapeutic area, including infectious diseases, hematology, oncology, pediatrics, cardiology, central nervous system disease, neurology, gastroenterology, hepatology, urology, infertility, ophthalmology, nephrology, orthopedics, pain control, psychiatry, pulmonology, vaccines, wound healing, physiology, pharmacology, dermatology, gene therapy, toxicology, and immunology.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore are not to be construed as limiting in any way the remainder of the disclosure.

Example 1

Electrospun Poly(N-Isopropyl Acrylamide)/Poly(Caprolactone) Fibers for the Generation of Anisotropic Cell Sheets Cell alignment in muscle, nervous tissue, and cartilage is requisite for proper tissue function; however, cell sheeting techniques using the thermosensitive polymer poly(N-isopropyl acrylamide) (PNIPAAm) can only produce anisotropic cell sheets with delicate and resource-intensive modifications. Without wishing to be bound by any particular theory, it was hypothesized that electrospinning, a relatively simple and inexpensive technique to generate aligned polymer fibers, could be used to fabricate anisotropic PNIPAAm and poly(caprolactone) (PCL) blended surfaces that both support cell viability and permit cell sheet detachment via PNIPAAm dissolution. Aligned electrospun PNIPAAm/PCL fibers (0%, 25%, 50%, 75%, 90%, and 100% PNIPAAm) were electrospun and characterized. Fibers ranged in diameter from 1-3 µm, and all fibers had an orientation index greater than 0.65 (orientation index lower limit of 0 for random orientation; upper limit of 1 for perfect alignment). Fourier transform infrared spectroscopy was used to confirm the relative content of PNIPAAm and PCL. For advancing water contact angle and mass loss studies, only high PNIPAAm-content fibers (75% and greater) exhibited temperature-dependent properties like 100% PNIPAAm fibers, whereas 25% and 50% PNIPAAm fibers behaved similarly to PCL-only fibers. 3T3 fibroblasts seeded on all PNIPAAm/PCL fibers had high cell viability and spreading except for the 100% PNIPAAm fibers. Cell sheet detachment by incubation with cold medium was successful for 90% PNIPAAm fibers, which had a sufficient amount of PCL to allow cell attachment and spreading but not enough to prevent detachment upon PNIPAAm dissolution. This study demonstrates the feasibility of using anisotropic electrospun PNIPAAm/PCL fibers to generate aligned cell sheets that can potentially better recapitulate anisotropic architecture to achieve proper tissue function.

The materials and methods employed in these experiments are now described.

Fabrication PNIPAAm/PCL Fibers

For PNIPAAm-only fibers, PNIPAAm (300 000 Da, Scientific Polymer Products, Ontario, NY) was dissolved 20% (wt/v) in methanol (Fisher Chemical, Pittsburgh, PA), as previously described (Lee et al., 2016, Adv. Healthcare Mater., 5:781-785). For PCL-only fibers, PCL (80 000 Da, Sigma-Aldrich, St Louis, MO) was dissolved 10% (wt/v) in hexafluoroisopropanol (Sigma-Aldrich). For PNIPAAm/PCL fibers, PNIPAAm and PCL (at ratios of 9:1, 3:1, 1:1, and 1:3, respectively) were dissolved 12-18% (wt/v) in a 1:3 mixture of methanol and chloroform (Sigma-Aldrich). All polymer solutions were dissolved by continuous stirring until clear and homogenous. To electrospin, a syringe pump (New Era Pump Systems, Inc.) was used to dispense the polymer solutions from a 10 mL syringe with a 25 G blunted stainless steel needle at 2.0 mL h$^{-1}$ for the PCL-only solution and 1.0 mL h$^{-1}$ for all PNIPAAm-containing solutions. A high voltage supply (Gamma High Voltage, Ormond Beach, FL) was used to apply a charge of 5-15 kV (optimal charge determined for each solution, Table 1) to the needle to initiate jet formation. Fibers were deposited on a rotating grounded 7.6 cm diameter aluminum collector. To obtain aligned fibers, the collector was rotated at 2500-3200 rotations per minute (RPM, approximately 10.0-12.8 m s$^{-1}$). The working distance from the needle and to collector was set at 11 cm. PNIPAAm/PCL fibers are referred to by the percent PNIPAAm content (i.e., 75% PNIPAAm fibers comprise 75% PNIPAAm and 25% PCL). Similarly, "high PCL-content" refers to 0%, 25%, and 50% PNIPAAm and "high PNIPAAm-content" refers to 75%, 90%, and 100% PNIPAAm.

TABLE 1

| PNIPAAm content | Total Polymer (wt/vol) | Solvent | Charge (kV) |
|---|---|---|---|
| 0% | 10% | HFP | 4.5-6.5 |
| 25% | 12% | 1:3 methanol:chloroform | 7.0-10.5 |
| 50% | 12% | 1:3 methanol:chloroform | 8.5-9.5 |
| 75% | 15% | 1:3 methanol:chloroform | 9.0-10.0 |
| 90% | 18% | 1:3 methanol:chloroform | 13.0-15.0 |
| 100% | 20% | methanol | 11.0-11.5 |

Characterization of PNIPAAm/PCL Fibers

Fiber Orientation and Diameter

PNIPAAm/PCL fibers were sputter coated with 12 nm platinum/palladium and imaged using a Zeiss Supra 40VP scanning electron microscope (SEM, 5 kV). SEM images (n=9) were analyzed using NIH ImageJ software, specifically the OrientationJ (Rezakhaniha et al., 2012, Biomech. Model. Mechanobiol., 11:461-473; Püspöki et al., 2016, Adv. Anat., Embryol. Cell Biol., 219:69-93) and Diameter) (Hotaling et al., 2015, Biomaterials, 61:327-338) plug-ins to determine fiber orientation and diameter, respectively. The fiber orientation index, S, was calculated from angle distribution histograms using the following equation: (Ferdman et al., 1993, J. Invest. Dermatol., 100:710-716)

$$S=2<\cos^2(\alpha)>-1$$

where $\alpha$ is the difference between an individual fiber angle and the mean angle of all fibers. S varies from 0 to 1, for perfectly random and perfectly aligned fibers, respectively.

Fourier Transform Infrared Spectroscopy

Fourier-transform infrared (FTIR) attenuated total reflectance (ATR) was used to verify fiber polymer composition. Spectra of dry PNIPAAm/PCL fibers was collected over a range of wavelengths (400 cm$^{-1}$ to 3000 cm$^{-1}$) at a resolution of 2 cm$^{-1}$ using a Thermo Scientific Nicolet iS10 FT-IR spectrometer (Waltham, MA). Background spectra was collected prior to each individual sample.

PNIPAAm Mass Loss

PNIPAAm/PCL fibers were cut (approximately 1 cm×1 cm, n=3) and weighed before being immersed in ultrapure water at room temperature. To ensure complete PNIPAAm dissolution, fibers were rinsed 3 times in 2 mL of water over 24 hours. Fibers were then dried under vacuum for 48 hours before measuring their final weight. Percent mass lost was determined by subtracting the final weight from the original weight. Fibers were imaged before and after rinsing, and original and post-dissolution areas were calculated in ImageJ. Percent contraction was determined by dividing the final area by the original area.

Advancing Contact Angle Measurement

Advancing contact angles were measured using a FTA-200 goniometer (First Ten Angstroms, Portsmouth, VA) to determine the relative hydrophobicity of dry (non-wetted) and wetted PNIPAAm/PCL fibers. Fibers were cut into squares (approximately 1.75 cm×1.75 cm, n=3). Wetted PNIPAAm/PCL fiber squares were secured in CellCrown inserts and rinsed in water warmed to 37° C. for 24 hours. Fibers were then dried in a vacuum oven at 35-55°, above the LCST of PNIPAAm and below the melting temperature of PCL. PNIPAAm/PCL fibers were placed on a heating platform to maintain the temperature between 32-60° C., as measured by an infrared thermometer for advancing water content angle analysis. Briefly, a drop of purified water was deposited at 0.8 µL per second from a 10 mL syringe on the PNIPAAm/PCL fibers, and high resolution images were subsequently captured. When possible, the contact angle was determined in the sessile drop session mode in the instrument-associated software. Otherwise, advancing contact angle was calculated by manually defining the location of the fiber plane and the drop's curvature.

Cell Studies

All cell studies were performed using NIH 3T3 fibroblasts purchased from American Type Culture Collection (Manassas, VA), passages 15-25. 3T3 fibroblasts were maintained in 10% fetal bovine serum (ThermoFisher) and 1% penicillin/streptomycin (ThermoFisher) in low glucose Dulbecco's Modified Eagle's Medium with L-glutamine (Sigma-Aldrich). 3T3 fibroblasts were passaged using trypsin/EDTA (Sigma-Aldrich).

PNIPAAm/PCL Fiber Sterilization and Protein Coating

Figure 10:
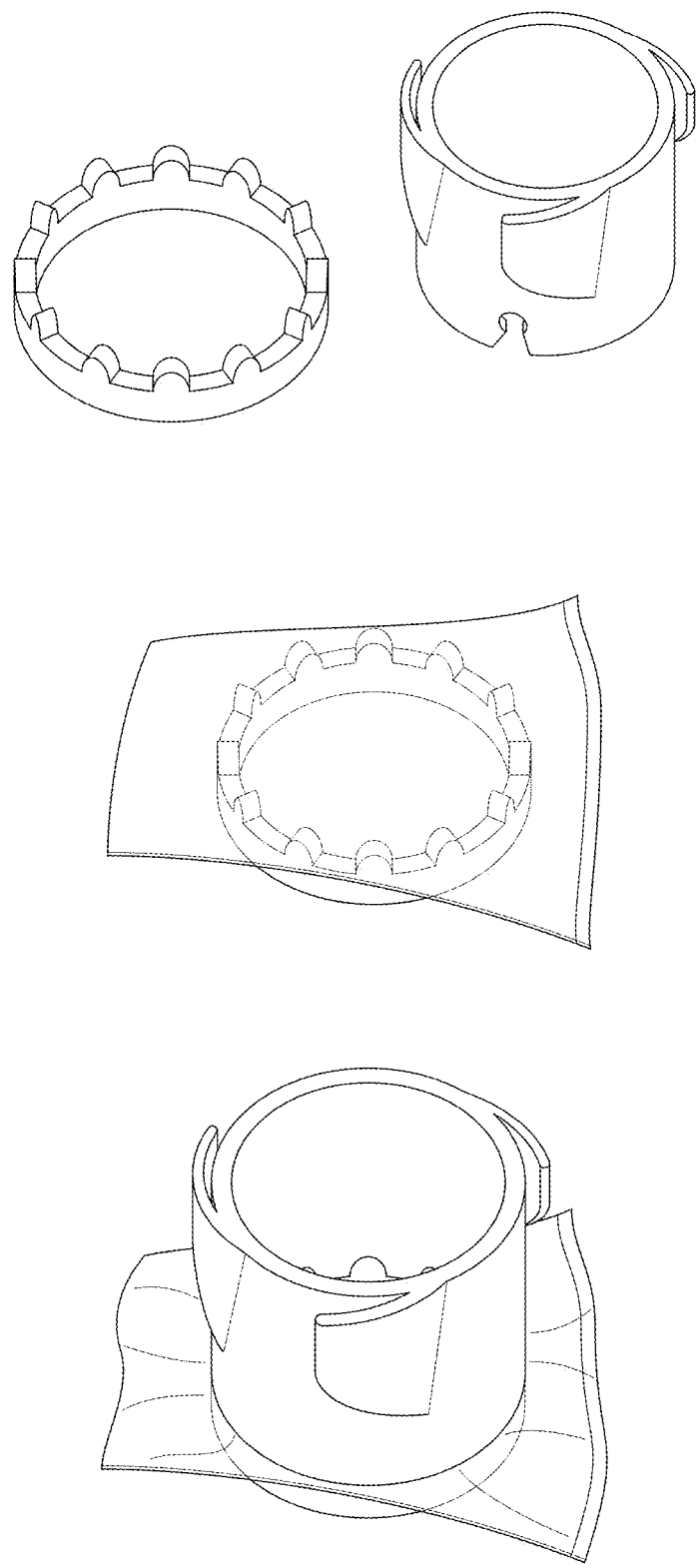
FIG. 10 depicts the construction of stand-alone PNIPAAm/PCL fiber bottom wells.

PNIPAAm/PCL fibers and parafilm were cut into squares (1.75 cm×1.75 cm or 2.5 cm×2.5 cm) and sterilized by ultraviolet light, 30 minutes each side. Fibers were secured using 12-well or 24-well CellCrown inserts (Scaffdex, Tampere, Finland) and parafilm (Bemis, Oshkosh, WI)—effectively making stand-alone PNIPAAm/PCL fiber bottom wells (FIG. 10)—to improve handling and prevent PNIPAAm fiber contraction upon wetting. Prior to coating, fibers were wetted with Dulbecco's Phosphate Buffered Saline (DPBS). Fibers were then coated with a 1:50 dilution of Growth-factor Reduced (GFR)-Matrigel (Corning, Corning, NY) in Dulbecco's Modified Eagle's Medium (DMEM). Fibers were also pre-treated with fetal bovine serum (FBS, ThermoFisher) for at least 10 minutes immediately prior to cell seeding, as recommended by Haraguchi et al. (Haraguchi et al., 2012, Nat. Protoc., 7:850-858). All solutions were warmed to 37° C. and fibers were kept on a hot plate in the tissue culture hood to ensure that PNIPAAm remained above its LCST.

Cell Viability on PNIPAAm/PCL Fibers

3T3 fibroblasts were seeded onto PNIPAAm/PCL fibers (n=3) at 120,000 cells per $cm^2$. This cell density was selected to ensure that the absorbance for the colorimetric assay was in the linear range. 24 hours post-seeding, cells were rinsed and treated with the tetrazolium dye 3-(4,5-dimethylthiazol-2-yl)-5-(3-carboxymethoxyphenyl)-2-(4-sulfophenyl)-2H-tetrazolium (MTS, CellTiter 96® AQueous One Solution Cell Proliferation Assay, Promega, Madison, WI). Solution absorbance was measured at 490 nm on a Biotek Cytation 3 Cell Imaging Multi-Mode Reader. Each condition was normalized by solution absorbance of 3T3 fibroblast-seeded PCL-only controls to determine relative cell attachment.

Cell Alignment on PNIPAAm/PCL Fibers

3T3 fibroblasts were seeded onto PNIPAAm/PCL fibers at 240,000 cells per $cm^2$. 24 hours post-seeding, cells on PNIPAAm/PCL fibers were rinsed and fixed in 4% (v/v) paraformaldehyde for 15 minutes. Cells were permeabilized with 0.2% (v/v) Triton X-100 for 10 minutes and then stained with 6.6 µM rhodamine phalloidin (ThermoFisher). Following actin staining, cell nuclei were stained with 300 nM 4',6-diamidino-2-phenylindole (DAPI, ThermoFisher). All solutions were warmed to and fibers were incubated at 37° C., above PNIPAAm's LCST, as described previously (Takahashi et al., 2011, Biomaterials, 32:8830-8838). Cell-seeded fibers were dissembled from CellCrown inserts, placed on slides, and imaged on a Biotek Cytation 3 Cell Imaging Multi-Mode Reader incubated to 37° C. Actin images were analyzed using NIH ImageJ software and OrientationJ plug-in to determine cell alignment.

Cell Sheet Detachment from PNIPAAm/PCL Fibers

3T3 fibroblasts were seeded onto PNIPAAm/PCL fibers at 630,000 cells per $cm^2$ and allowed to grow for 4 days. Medium was changed every day. Prior to detachment, cells were stained with 5 µM calcein, AM (ThermoFisher) and nuclear stain Hoescht 33342 (ThermoFisher) for 30 minutes. Detachment was initiated by rinsing 5 times over 10-15 minutes with cold (approximately 4° C.) medium to dissolve and remove PNIPAAm. Cell sheets were rinsed from the CellCrown insert with additional medium and imaged on an Olympus IX83 fluorescent microscope.

Statistical Methods

All data are presented as mean±standard deviation. Statistical significance was calculated by performing one-way ANOVA analysis followed by Tukey's multiple comparison in GraphPad, Prism Software. Differences are considered significant for $p<0.05$.

The results of the experiments are now described.

Characterization of PNIPAAm/PCL Fibers

Figure 1B:
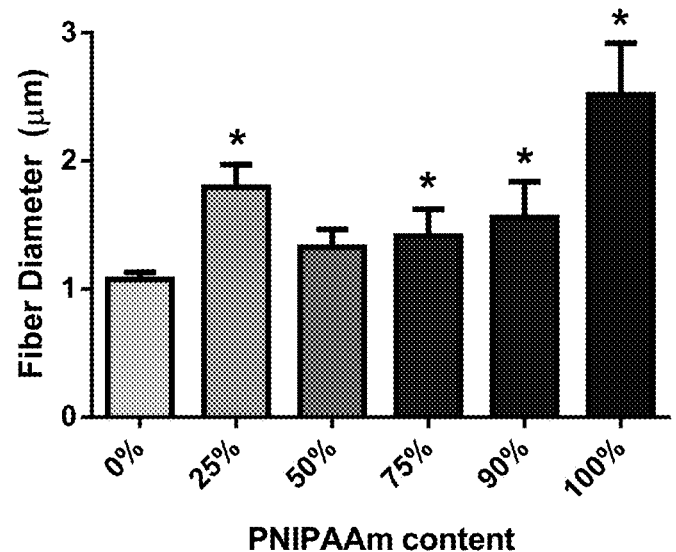
Figure 1C:
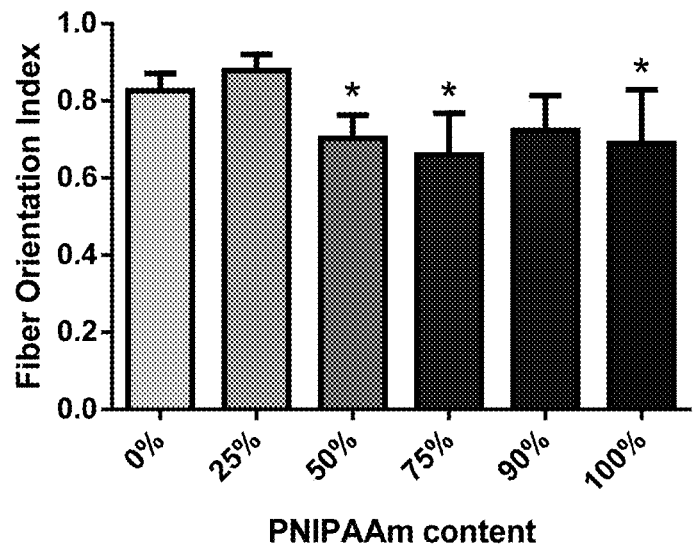

To generate PNIPAAm/PCL co-fibers, a solvent combination—methanol and chloroform—that dissolves both PNIPAAm and PCL was identified by referring to previous reports on PCL solubility in electrospinning solvents (Bordes et al., 2010, Int. J. Pharm., 383:236-243). SEM imaging confirmed fiber formation (FIG. 1A). Eletrospinning PCL-only and PNIPAAm-only fibers in methanol and chloroform was attempted; however, fiber formation and alignment was poor compared to the PNIPAAm/PCL blended fibers. Consequently, PCL-only and PNIPAAm-only fibers were electrospun using HFP and methanol, respectively, following previous reports (Lee et al., 2016, Adv. Healthcare Mater., 5:781-785; Nam et al., 2008, J. Appl. Polym. Sci., 107:1547-1554). Interestingly, only the 100% PNIPAAm fibers exhibited a flat, ribbon-like morphology, as was previously reported for PNIPAAm fibers electrospun by Rockwood et al (Rockwood et al., 2008, Polymer, 49:4025-4032). Average fiber diameters ranged from 1 to 3 µm, with PCL-only fibers being the smallest diameter and PNIPAAm-only fibers having the largest diameter (FIG. 1B). Orientation analysis confirmed fiber alignment, with all conditions having an orientation index greater than 0.65, with 0% and 25% PNIPAAm fibers having significantly greater orientation indices than fibers containing 50% or more PNIPAAm (FIG. 1C). Differences in diameter and fiber orientation between PCL-only, PNIPAAm-only, and the PNIPAAm/PCL fibers may be attributable to the solvent of choice, which affects solution viscosity—a parameter known to largely determine fiber diameter (Thompson et al., 2007, Polymer, 48:6913-6922). Furthermore, the solution viscosity is also influenced by the relative amounts of PNIPAAm and PCL, as their respective molecular weights, effective chain lengths, and solubility in methanol and chloroform differ. It was observed that higher PCL-content fibers could be electrospun from solutions for which the combined polymer concentration of the solution was lower (Table 1). For example, 90% PNIPAAm fibers were electrospun from a solution of 18% (wt/v) of 9:1 PNIPAAm:PCL whereas 25% PNIPAAm fibers were electrospun from a solution of 12% (wt/v) of 1:3 PNIPAAm: PCL.

Figure 2A:
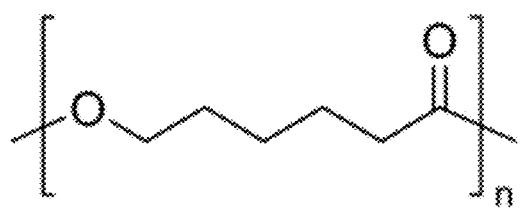
FIG. 2A through FIG. 2C depict results from example experiments demonstrating chemical structures and Fourier Transform Infrared spectroscopy (FTIR) results. Depicted are chemical structures of (FIG. 2A) PCL and (FIG. 2B) PNIPAAm.
Figure 2B:
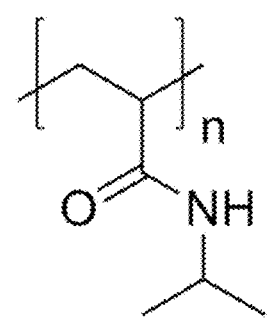
Figure 2C:
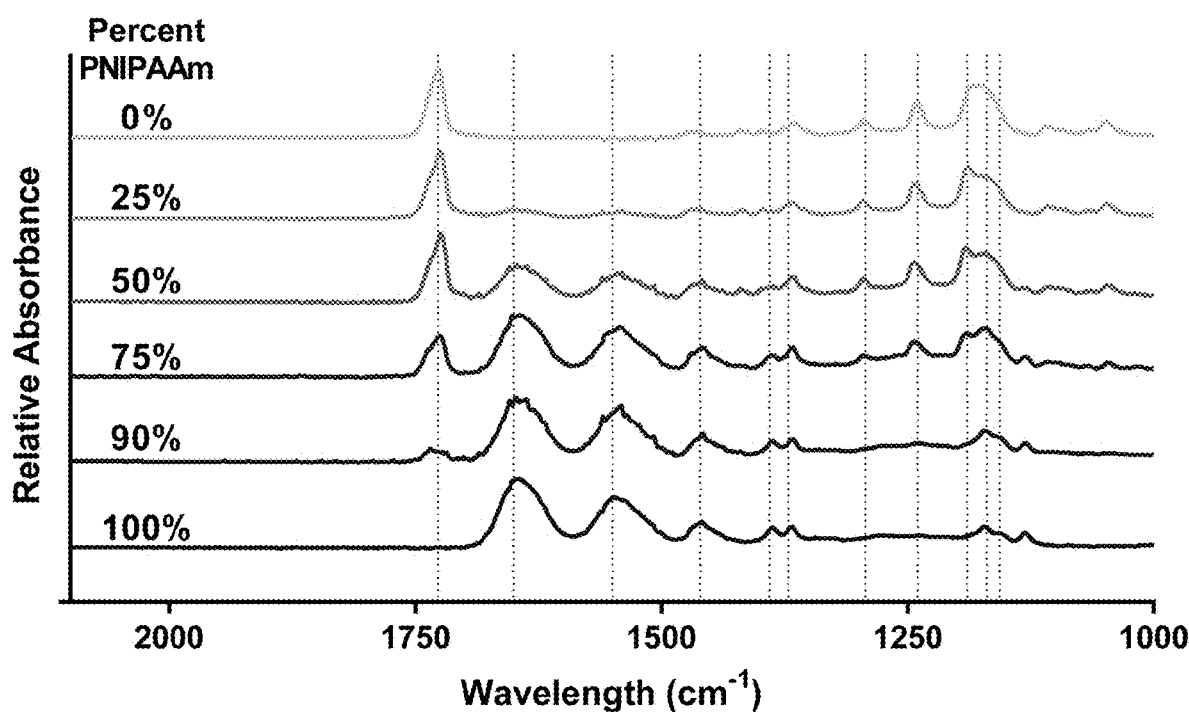

FTIR spectroscopy confirmed that relative polymer compositions of PNIPAAm/PCL fibers followed the starting PNIPAAm concentration (FIG. 2C), as PCL-specific peaks increased with PCL-content and PNIPAAm-specific peaks increased with PNIPAAm content. The PCL-only (0% PNIPAAm) fibers show a strong peak at 1727 $cm^{-1}$ indicating carbonyl stretching, which is reduced as PNIPAAm content increases and is absent for the 100% PNIPAAm fibers. Similarly, PNIPAAm-only fibers (100% PNIPAAm) show strong peaks at 1626 and 1559 $cm^{-1}$ for amide group vibrations that become less strong as PNIPAAm content decreases and are completely absent for the 0% PNIPAAm fibers. Additional absorbance peaks for each polymer are listed in FIG. 7 (Beattie et al., 2014, Phys. Chem. Chem. Phys., 16:25143-25151; Elzein et al., 2004, J. Colloid Interface Sci., 273:381-387; Dybal et al., 2009, Vib. Spectrosc., 51:44-51).

Figure 3A:
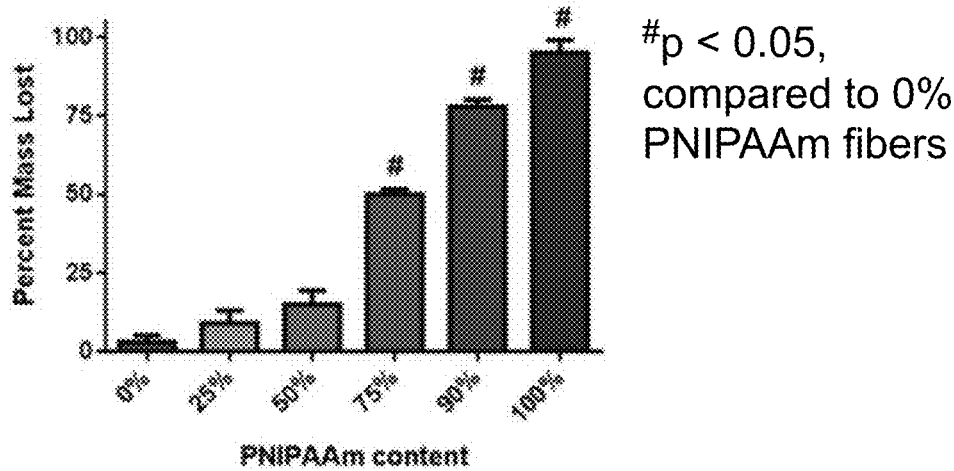
FIG. 3A through FIG. 3C depict results from example experiments demonstrating PNIPAAm dissolution from PNIPAAm/PCL fibers.
Figure 3B:
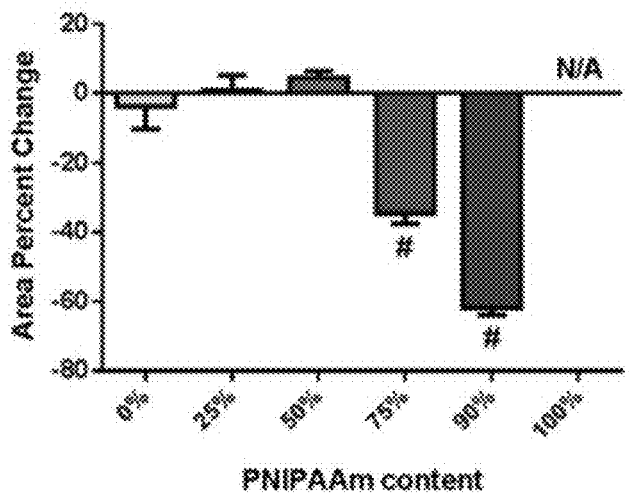
Figure 3C:
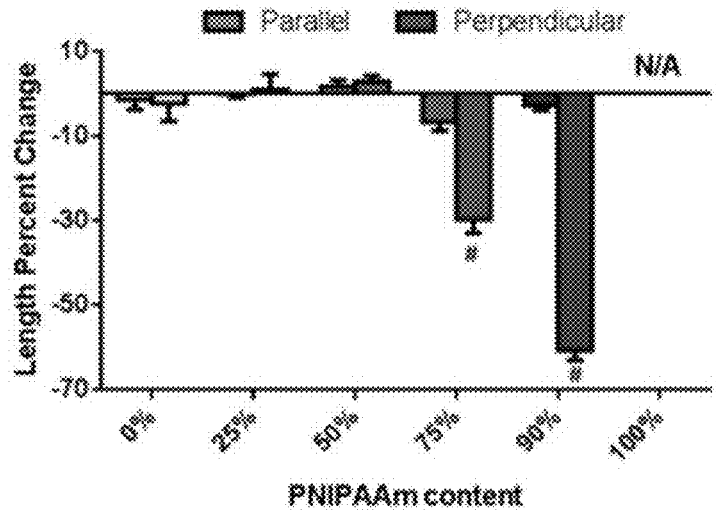
Figure 11:
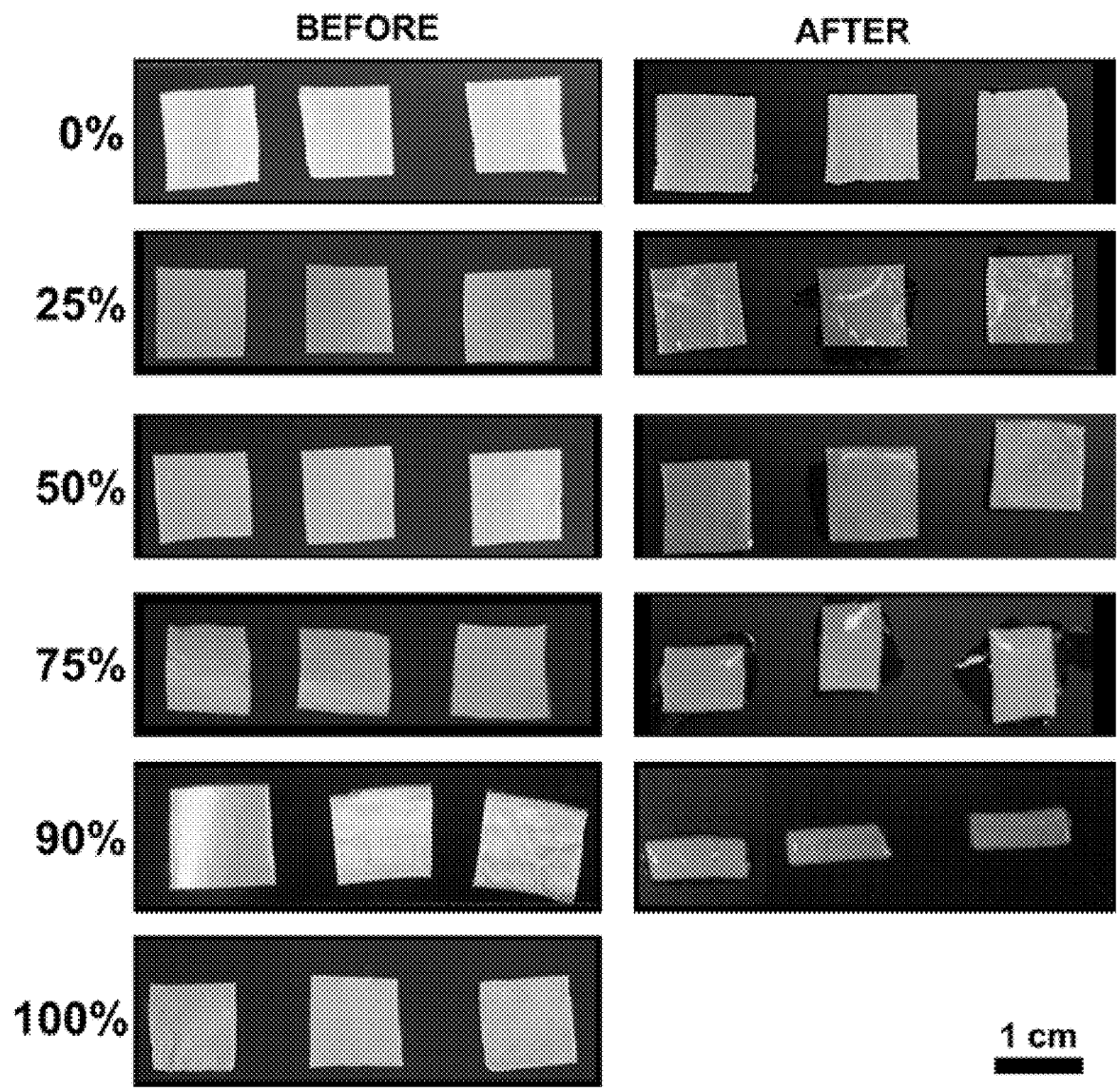
FIG. 11 depicts a series of images of PNIPAAm/PCL fibers (at various percentage of PNIPAAM content) before and after wetting.

To further confirm relative PNIPAAm content and evaluate the potential of PNIPAAm/PCL fibers for cell sheet detachment via PNIPAAm dissolution, PNIPAAm/PCL fibers were immersed in room temperature (approximately 20° C.) water to dissolve out PNIPAAm (FIG. 3A through FIG. 3C). Fibers with a considerable amount of PCL showed little mass loss (less than 5% the original weight) whereas high-content PNIPAAm fibers lost more than 50% their original mass (FIG. 3A). Observations of PNIPAAm/PCL fiber area and axial length changes before and after wetting supported the mass loss data: high PNIPAAm-content fiber area contracted more than 55% whereas high PCL-content fibers did not contract but instead slightly swelled (FIG. 3B). Furthermore, 75% and 90% PNIPAAm fiber contraction was uniaxial, perpendicular to fiber orientation (FIG. 3C and FIG. 11). As expected, 100% PNIPAAm fibers completely dissolved, preventing measurements of mass loss and changes in area and axes length. For high PCL-content fibers, the percent mass lost does not match the starting percent PNIPAAm content, indicating that the PCL protects PNIPAAm from dissolving.

Figure 4A:
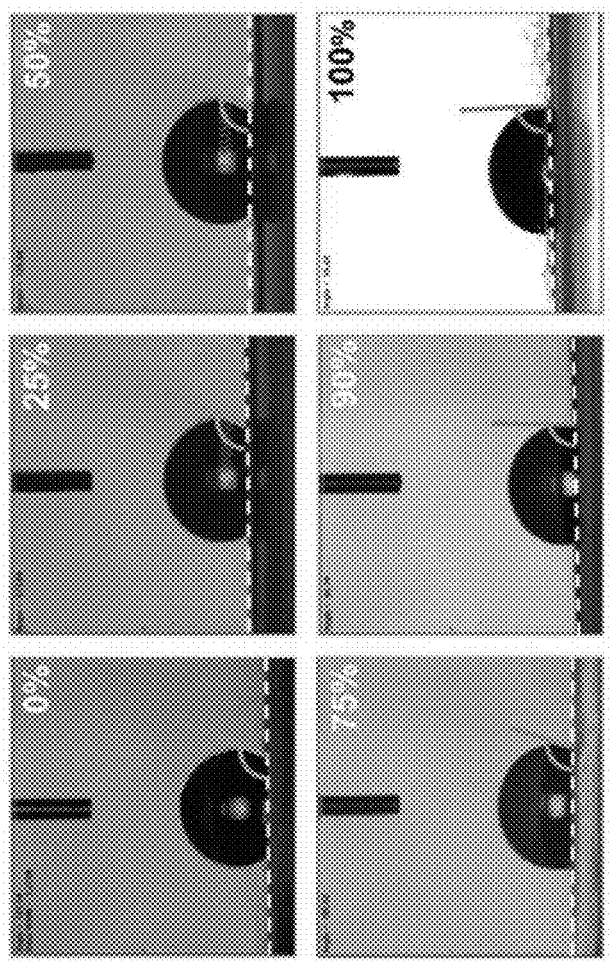
FIG. 4A and FIG. 4B depict results from example experiments demonstrating hydrophilicity of PNIPAAm/PCL fibers.
Figure 4B:
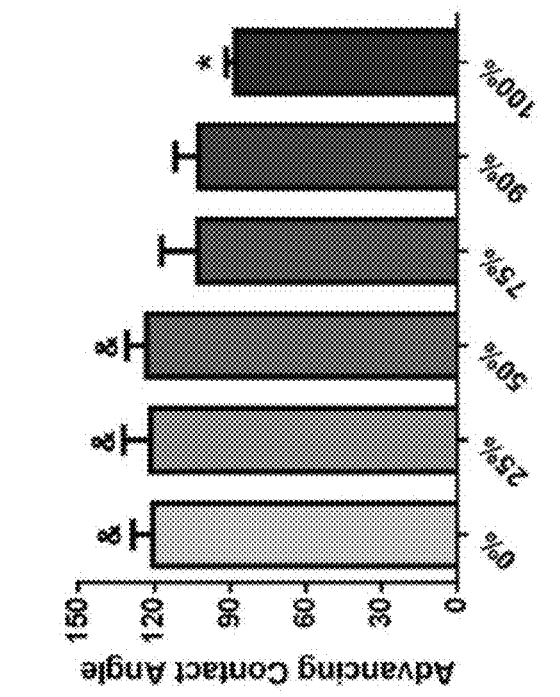
Figure 12:
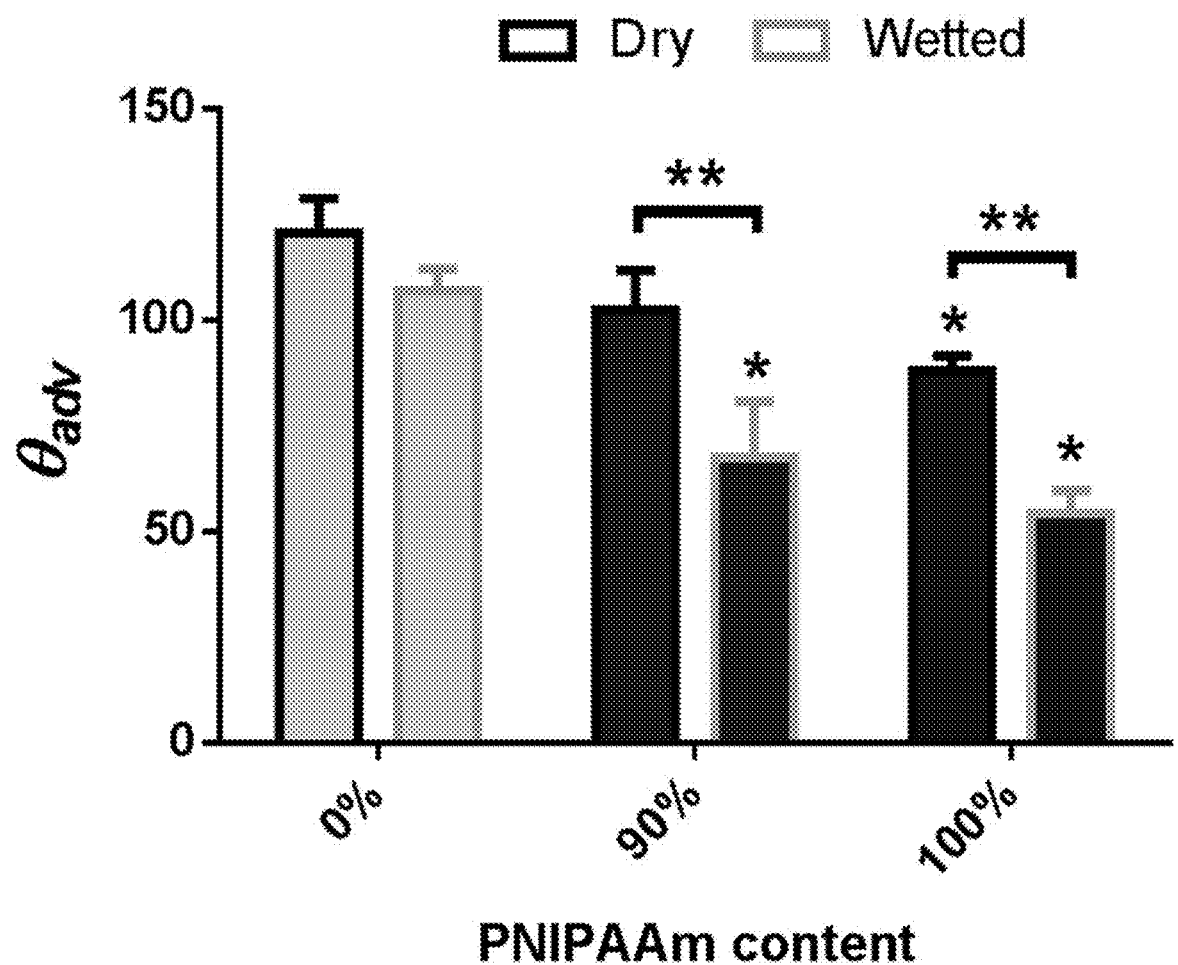
FIG. 12 depicts the results of experiments depicting the advancing water contact angle of dry and wetted PNIPAAm/PCL fibers at 0%, 90% and 100% PNIPAAm content.
Figure 13:
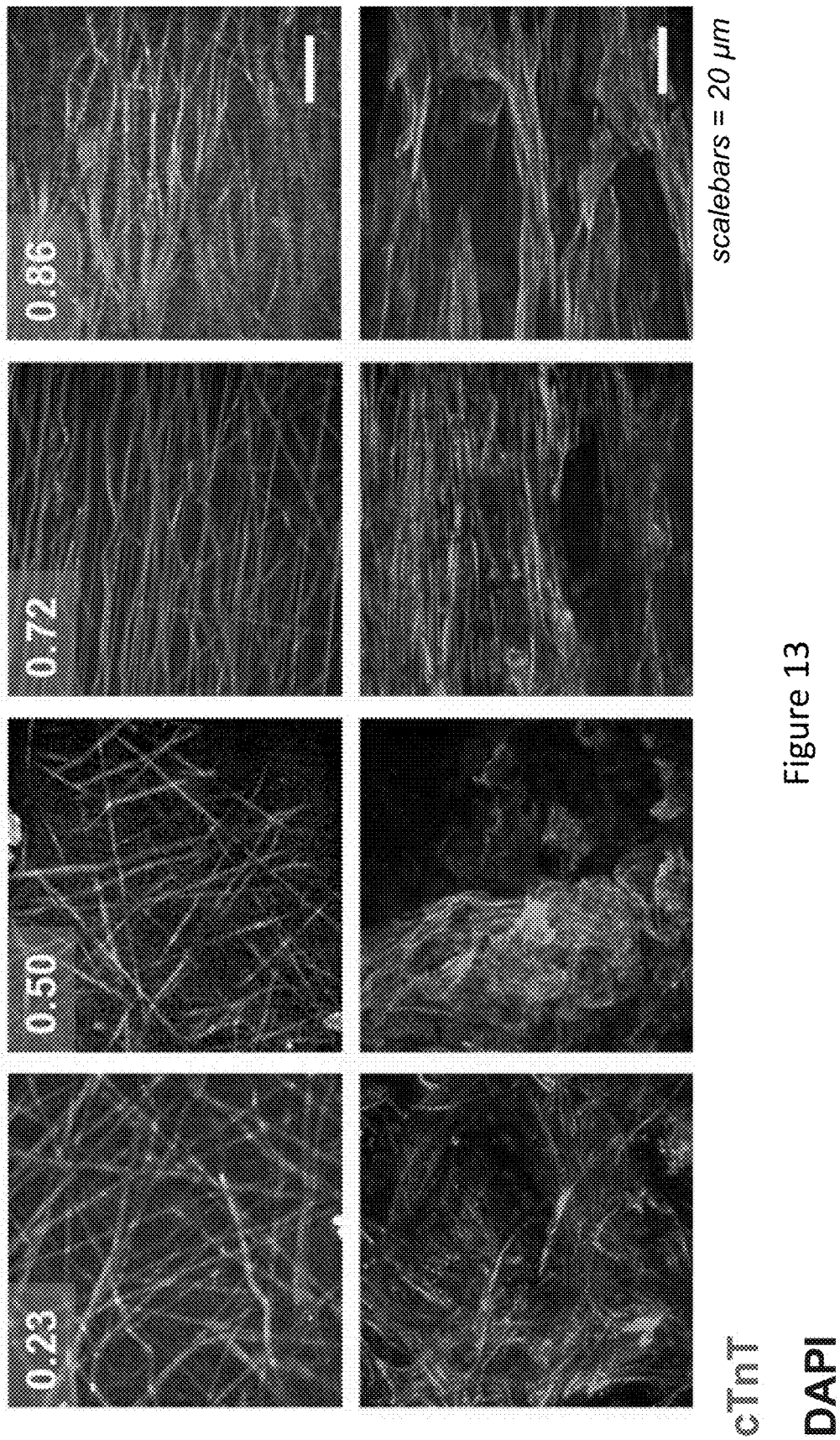
FIG. 13 depicts the results of experiments differentiating mouse embryonic stem cells (mESCs) into cardiomyocytes on PNIPAAm/PCL fiber sheets. The top row depicts four PNIPAAm/PCL fiber sheets having the same ratio of PNIPAAm:PCL (90:1). The number in the top left corner indicates the alignment scale from 0 (unaligned) to 1 (perfect parallel alignment). The bottom row depicts mESCs differentiated on the mats, with cTnT marker being used to identify differentiation into cardiac cells. Cell orientation is observed in cultures on mats having alignment scales above 0.50.

Relative hydrophobicity of the PNIPAAm/PCL fibers was determined by measuring advancing water contact angle above 32° C., showing that dry and wetted 100% PNIPAAm fibers ($\theta_{adv}$=88.0° and 55.3°, respectively) were significantly less hydrophobic than 0% PNIPAAm fibers ($\theta_{adv}$=120.7° and 107.1°, FIG. 4A, FIG. 4B, and FIG. 12). In fact, all dry, high PCL-content fibers (0%, 25%, 50% PNIPAAm) were all significantly more hydrophobic than 100% PNIPAAm fibers with $\theta_{adv}$>120°. Because PNIPAAm undergoes a coil-to-globule transition at its LCST, it does not become truly hydrophobic above its LCST; rather, the hydrophobic domains are exposed to the aqueous solution, enabling protein adsorption (Pelton, 2010, J. Colloid Interface Sci., 348:673-674). Evaluations of relatively thick and thin layers of PNIPAAm-grafted surfaces found that Oath, decreased with thickness, meaning thicker PNIPAAm surfaces were less hydrophobic (Yamato et al., 2007, Prog. Polym. Sci., 32:1123-1133). Because biomaterial hydrophobicity is an indicator of the degree of protein adsorption, low hydrophobicity may impair cell attachment and spreading.

The mass loss, area contraction, and advancing water contact angle data are largely consistent in that the high PCL-content fibers behave similarly and that significant differences are observed for high PNIPAAm-content fibers. Significant mass loss and area contraction from PNIPAAm dissolution starts to occur with 75% PNIPAAm. A possible explanation for these data is that the PNIPAAm/PCL fibers may have a core-sheath architecture, with a PNIPAAm core and PCL sheath. This has been previously observed for PNIPAAm and PCL blended fibers electrospun in dimethylformamide (DMF) and chloroform, although with a PNIPAAm sheath around a PCL core (Chen et al., 2010, Chem. Mater., 22:4214-4221). Chen et al. proposed a thermodynamic argument: because DMF was a better solvent for PNIPAAm than for PCL and because DMF had a much lower boiling point than chloroform, the DMF evaporated first, leaving PNIPAAm on the exterior. In the present example, methanol's boiling point (64.7° C.) is slightly higher than chloroform's boiling point (61.2° C.), and methanol is a good solvent for PNIPAAm but a bad solvent for PCL. Applying the same thermodynamic argument, the PCL should be dissolved in the chloroform portion, which would evaporate first to leaving PCL on the exterior of the fibers. For high PCL-content fibers, the PCL may form an entire sheath around the PNIPAAm; however, as PNIPAAm content increases, there would not be enough PCL to protect PNIPAAm from dissolution, as observed by the mass loss and contact angle data.

Cell Viability and Alignment on PNIPAAm/PCL Fibers

After confirming the relative PNIPAAm content, the behavior of NIH 3T3 fibroblasts on PNIPAAm/PCL fibers was assessed. Given PNIPAAm's relative low hydrophobicity as indicated by advancing water contact angle, PNIPAAm/PCL fibers were coated with a 1:50 GFR-Matrigel dilution and pre-treated fibers with FBS prior to seeding, as recommended by Haraguchi et al. (Haraguchi et al., 2012, Nat. Protoc., 7:850-858); other groups have combined PNIPAAm with gelatin (Zhao et al., 2016, J. Nanosci. Nanotechnol., 16:5520-5527), chitosan (Wang et al., 2009, J. Mater. Sci.: Mater. Med., 20:583-590), fibronectin (Takahashi et al., 2011, Biomaterials, 32:8830-8838; Akiyama et al., 2004, Langmuir, 20:5506-5511), collagen (Moran et al., 2007, J. Biomed. Mater. Res., 81A:870-876), poly-L-lysine, and laminin (Moran et al., 2007, J. R. Soc., Interface, 4:1151-1157) to improve cell adhesion.

Figure 5B:
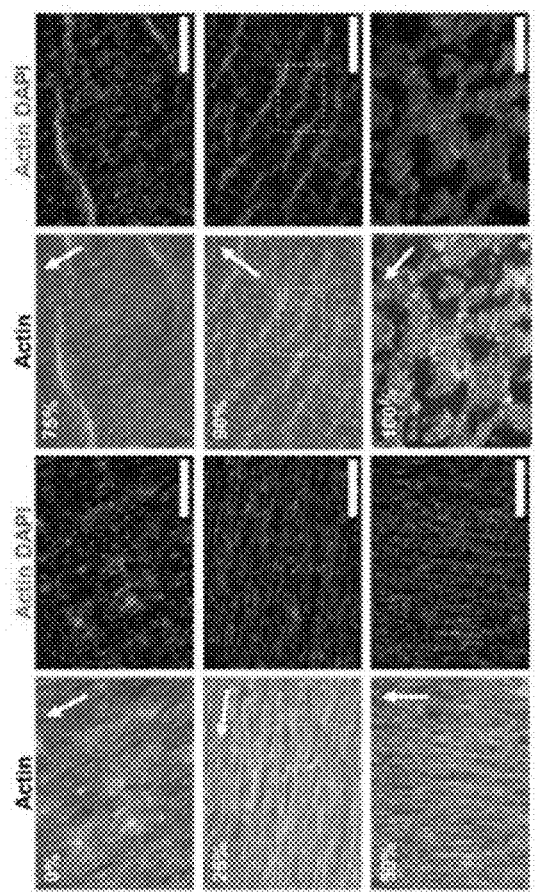
FIG. 5A through FIG. 5C depict results from example experiments demonstrating cell viability and cell alignment on PNIPAAm/PCL fibers.
Figure 5C:
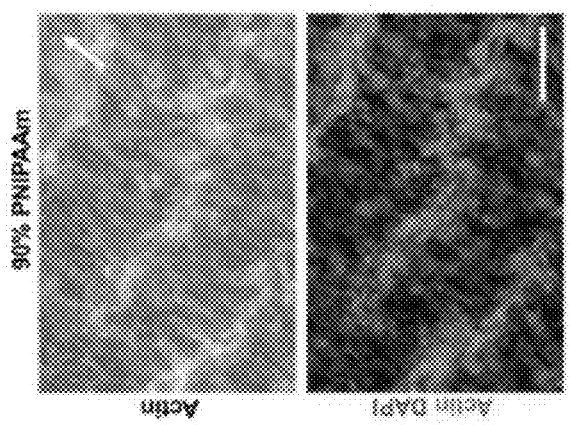
Figure 5A:
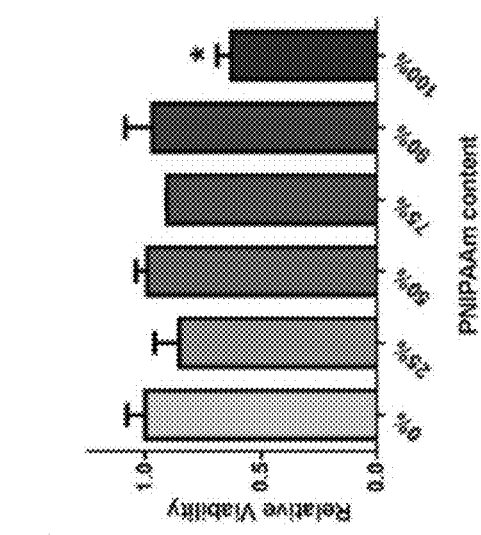
Figure 8:
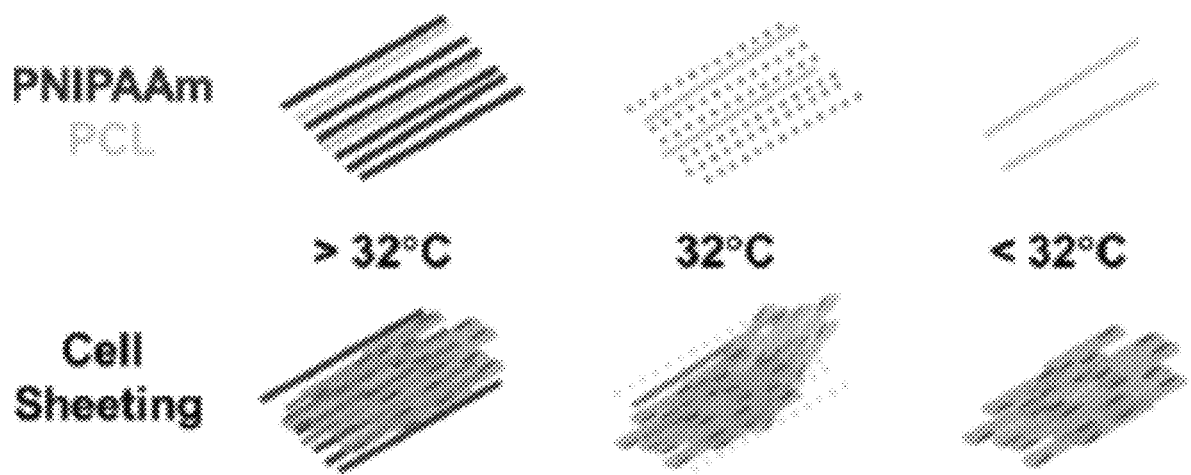
FIG. 8 depicts an illustration summarizing PNIPAAm/PCL fibers and cell sheeting, under various temperature conditions.
Figure 9:
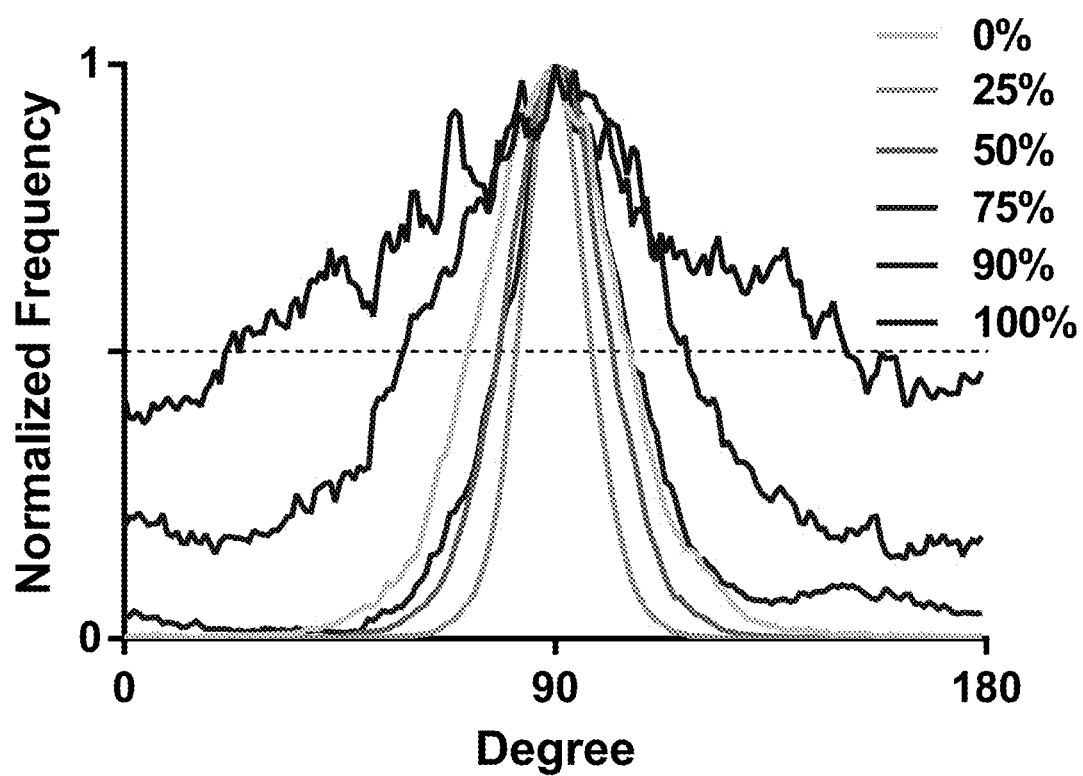
FIG. 9 depicts results from example experiments demonstrating the normalized frequency plotted as a function of the cell orientation degree. 3T3 fibroblasts were seeded on PNIPAAm/PCL fibers, grown for 24 hours, and then stained with phalloidin to visualize actin. Images were analyzed in Image J to determine cell orientation. Cells were spread and clearly aligned on PNIPAAm/PCL fibers but not on 100% PNIPAAm fibers.

MTS assay 24-hours post-seeding demonstrated that cells attached and were viable on PNIPAAm/PCL fibers as compared to the PCL-only (0% PNIPAAm) control (FIG. 5A through FIG. 5C). However, cells were significantly less viable (60% relative to PCL-only control) on 100% PNIPAAm fibers. To visualize cytoskeletal actin, cells were stained with rhodamine phalloidin 24-hours post-seeding on PNIPAAm/PCL fibers. Fibers containing PCL (0%, 25%, 50%, 75%, and 90% PNIPAAm) showed robust spreading and significant cell alignment in a preferred direction (FIG. 5B and FIG. 5C). On 100% PNIPAAm fibers, cells showed notably less spreading and grew in clusters, which is in line with the relatively poor cell viability observed on these fibers. As PNIPAAm is clearly not toxic to cells, as indicted by comparable cell viability on 0%, 25%, 50%, 75%, and 90% PNIPAAm fibers, it is likely that cell attachment was affected by poor adhesion protein adsorption due to its decreased hydrophobicity. This is consistent with the advancing water contact results and previous reports that protein adsorption onto PNIPAAm, especially thick PNIPAAm films (>15-20 nm), is severely limited (Akiyama et al., 2004, Langmuir, 20:5506-5511; Moran et al., 2007, J. R. Soc., Interface, 4:1151-1157). Understandably, coating with cell adhesion proteins (Haraguchi et al., 2012, Nat. Protoc., 7:850-858) and grafting gelatin to PNIPAAm (Zhao et al., 2016, J. Nanosci. Nanotechnol., 16:5520-5527) has been used to improve cell attachment to and spreading on PNIPAAm surfaces. Representative histograms of cell angle show that cells had relatively high alignment on high-content PCL fibers (FIG. 9). Although less aligned, cells on 75% and 90% PNIPAAm fibers had a preferred angle to which the cells aligned. The actin ridges that appeared on 75% and 90% PNIPAAm fibers is likely due to PNIPAAm contracture as the fibers had to be removed from the Cell-Crown inserts for imaging. This phenomenon affected the orientation analysis as these ridges, which are perpendicular to cell orientation angle, dampened the preferred cell angle peak.

Cell Sheet Detachment

Detachment of aligned fibroblast cell sheets was attempted by incubating cell-seeded PNIPAAm/PCL fibers in cold medium. Following previous reports on cell sheeting (Takahashi et al., 2011, Biomaterials, 32:8830-8838; Haraguchi et al., 2012, Nat. Protoc., 7:850-858) cells were seeded at an ultra-high density—630,000 cells per $cm^2$—to ensure sufficient cell-cell adhesion and ECM deposition. Detachment was initiated by rinsing cell-seeded PNIPAAm/PCL fibers with cold medium to dissolve the PNIPAAm. Cell sheet detachment from PNIPAAm/PCL fibers was successful for 90% PNIPAAm fibers (FIG. 6A), which occurred rapidly (less than 15 minutes). For lower PNIPAAm-content fibers, too much PCL remained preventing cell detachment. Cell sheet detachment from 100% PNIPAAm fibers was unsuccessful because the cells did not form a complete monolayer, as indicated by the cell morphology data (FIG. 5B). Cell sheets exhibited slight curling at the edges, evidenced by the thickening around the edges. Calcein staining confirmed that cell sheets were viable, intact, and consisted of aligned cells (FIG. 6B and FIG. 6C). Compared to previous reports of anisotropic cell sheeting from anisotropic PNIPAAm surfaces (Takahashi et al., 2011, Biomaterials, 32:8830-8838; Zhao et al., 2016, J. Nanosci. Nanotechnol., 16:5520-5527) relatively little contraction of the cell sheet was observed. This may be due to the presence of residual PCL, which can be observed in phase contrast images of the cell sheets (FIG. 6D and FIG. 6E).

The present data demonstrate that electrospun PNIPAAm/PCL fibers can be used to culture aligned cells, and that 90% PNIPAAm fibers can be used for cell detachment. This follows the original hypothesis that PNIPAAm and PCL have complementary roles and must be present in sufficient amounts. PCL encourages cell attachment, but too much PCL precludes cell sheet detachment. Likewise, PNIPAAm's low hydrophobicity limits for cell attachment but is necessary for cell sheet detachment. The cell sheets generated by the present method did show some contraction. Gelatin hydrogel plungers have been previously used to prevent cell sheet contracture and could easily be used in conjunction with the present PNIPAAm/PCL fibers (Haraguchi et al., 2012, Nat. Protoc., 7:850-858). 3T3 fibroblasts were used as a proof of principle to demonstrate that PNIPAAm/PCL fibers can generate cell sheets. The present system can be used with other cell types to possibly generate more complex tissue structures, such as blood vessels with better cellular architecture of the tunica media. Thus, electrospun PNIPAAm/PCL fibers, which are simple and relatively inexpensive to produce, have the potential to be used to generate anisotropic cell sheets that can either enable analyses that are typically precluded by the use of plates or biomaterial scaffolds or be used to create tissue-like constructs for in vivo transplantation (Shimizu et al., 2002, Circ. Res., 90:e40; Yang et al., 2007, Biomaterials, 28:5033-5043).

In summary, a simple, inexpensive, and low-resource system to generate cell sheets has been developed. PNIPAAm and PCL were successfully electrospun to generate aligned PNIPAAm/PCL blended fibers on which 3T3 fibroblasts were cultured. Cell viability and cell alignment was observed on PCL and PNIPAAm/PCL fibers whereas cell viability and cell alignment was impaired on 100% PNIPAAm fibers. Detachment of viable cell sheets by incubation with room temperature medium was successful for 90% PNIPAAm fibers; cell sheets did not detach from fibers containing less PNIPAAm and cells did not form a contiguous monolayer on 100% PNIPAAm.

Example 2

Cardiac Differentiation on PNIPAAm/PCL Fibers for Cardiac Cell Sheeting

Mouse embryonic stem cells (mESCs) were differentiated to cardiomyocytes (CMs) on select PNIPAAm/PCL fibers, were characterized for contractile and electrophysiological function, and were compared with CMs differentiated on unaligned PNIPAAm/PC fibers and 2D mESC-derived CM monolayers as controls. MHC+ mESCs were used to facilitate CM visualization.

Cardiac Differentiation

A comprehensive analysis is conducted for expression of Sarcomeric/cytoskeletal genes (MYH6, MYH7, MYL2, MYL7, TNNT2, TNNI3, ACTN2), calcium-handling genes (CASQ2, RYR2, SLC8A1, ATP2A3, ATP2A2, PLN), ion channels (CACNA1C, HCN4, KCNJ2, KCNJ3), and transcription factors (GATA4, NKX2.5) by qRT-PCR at early and late time points (days 12 and 24, respectively) to evaluate relative maturity (n=3/group with 2 technical replicates).

Cell Alignment

Cells on PNIPAAm/PCL fibers and on detached sheets are stained with anti-cardiac troponin T (cTnT) to visualize CM cytoskeletons, and images are analyzed in ImageJ to determine CM orientation before and after detachment (4 ROIs/sample, n=3). Differences in cell alignment have been observed on aligned and unaligned fibers as cells differentiate. Fibers are stained with fluorescein-conjugated gelatin prior to cell seeding to confirm that cell orientation follows fiber orientation (4 ROIs/sample, n=3).

Contractility

Figure 16A:
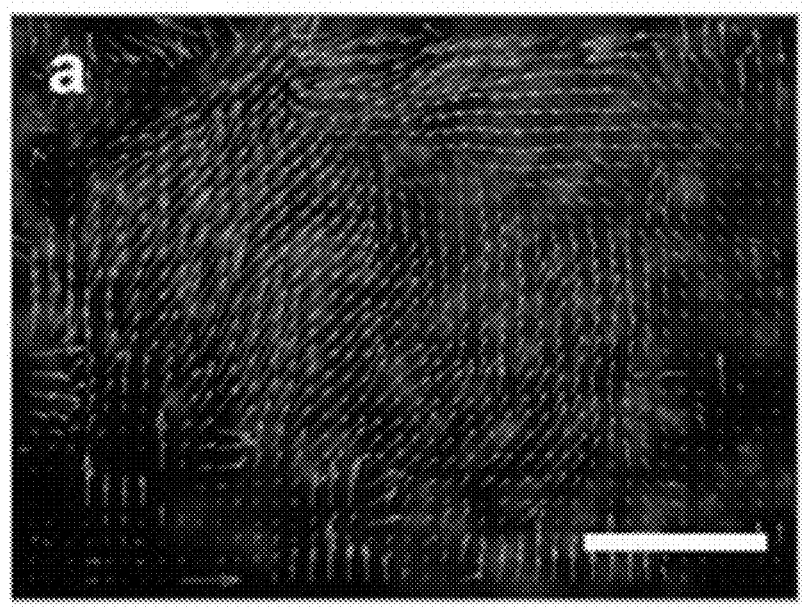
FIG. 16A depicts a time series image analyzed in PIVlab showing motion vectors for the contraction directionality of mCherry expressing mESCs differentiated into cardiomyocytes on aligned PCL fibers.
Figure 16B:
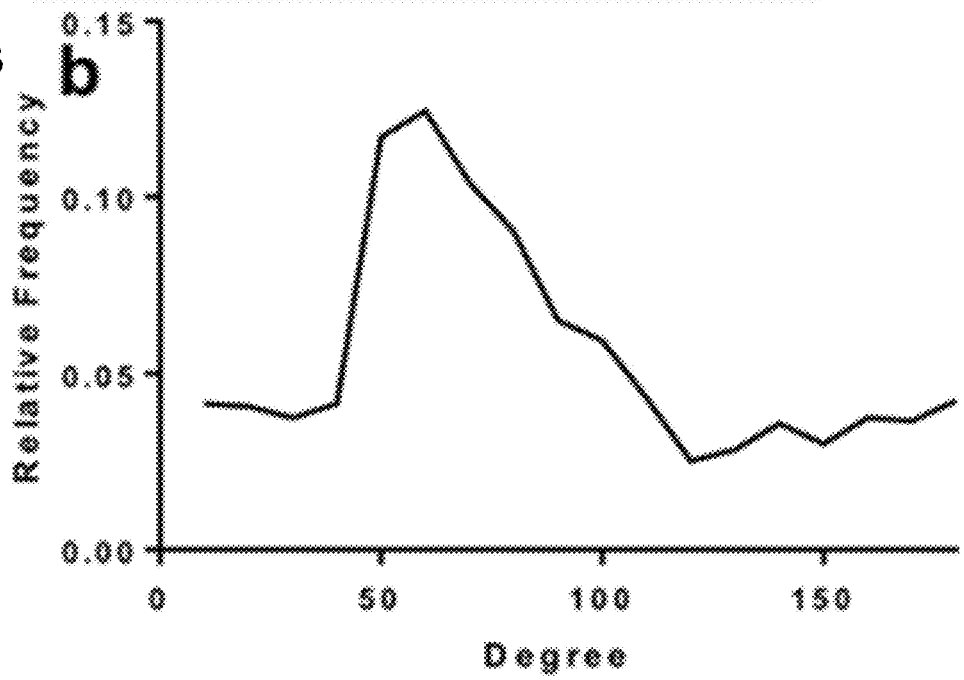
FIG. 16B is a chart quantifying the relative frequency of each cardiomyocyte contraction direction, demonstrating that on aligned fibers, cardiac contraction has a preferred contraction direction, which is the fiber direction.

Brightfield or fluorescent time series images of CMs (aligned and non-aligned cardiac cell sheets at 24 hours post-detachment and age-matched monolayers) are analyzed using PIVlab (an open source MATLAB application analyzing particle image velocimetry) to determine contraction/relaxation velocities, contraction direction, and magnitude, similar to other published work (Lee S et al., Biomaterials, 2017, 131:11-20) (4 ROIs/sample, n=3/group). Using such analysis on time lapse images of mCherry-expressing CM differentiated on aligned PCL fibers, contraction directionality was observed (FIG. 16A, FIG. 16B). This approach allows for the measurement of contraction on the single cell level. For tissue level contraction, a custom build cantilever bending test is used (FIG. 17). Cell sheets are attached to a testing clamp and submerged in Tyrode's solution. Cardiomyocyte contraction changes the position of the cantilever, and this change in length is recorded. Changes in length can then be used to determine contraction forces (n=6). Preliminary data comparing changes in length of aligned and unaligned PCL seeded fibers showed that CMs contraction on aligned fibers caused a 10% displacement while unaligned seeded fibers had no detectable displacement above noise levels (evaluated by unseeded fiber controls).

Action Potential Propagation

Figure 14:
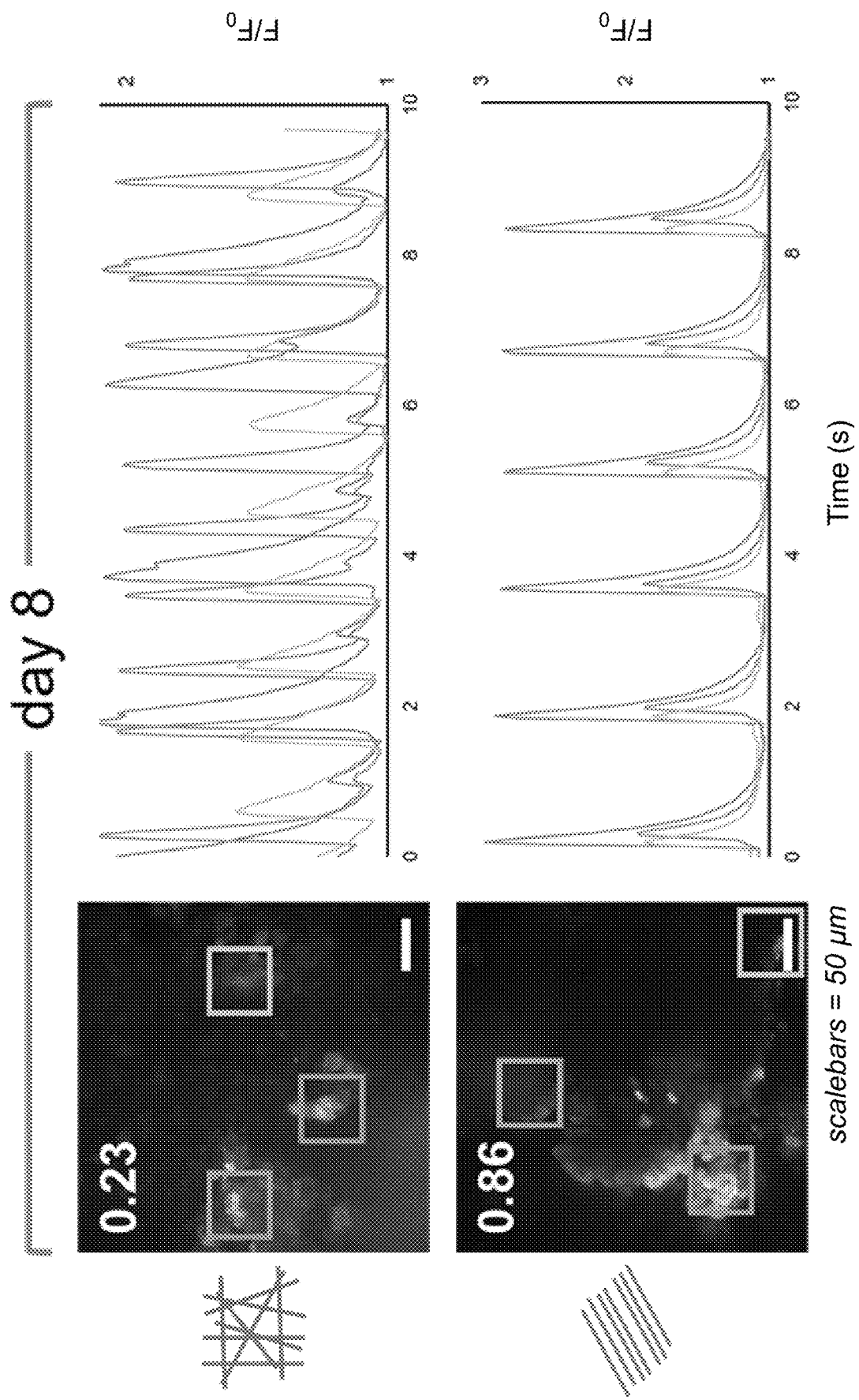
FIG. 14 depicts the results of experiments measuring the synchronization of mESCs differentiated into beating cardiomyocytes on PNIPAAm/PCL fiber sheets shown in FIG. 13. The top row shows an 8 day culture of mESCs on a PNIPAAm/PCL fiber sheet having an alignment scale of 0.23. The bottom row shows an 8 day culture of mESCs on a PNIPAAm/PCL fiber sheet having an alignment scale of 0.86. Beating is measured by fluorescent calcium reporter dye. The results demonstrate the differentiation on the highly aligned fiber sheet has synchronized beating.

To assess CM action potentials, intracellular calcium flux is monitored using the calcium-sensitive fluorophore Fluo-4, AM. Time-lapse images (up to 30 frames/second) are captured on an Axio Observer Z1 Spinning Disc confocal microscope; 3 regions of interest (ROIs) are analyzed to determine synchronicity for cells on non-aligned and aligned fibers. The data demonstrates that cell alignment promotes synchronized beating (FIG. 14). Further analysis in MAT-LAB determines percent beating area as well as action potential propagation velocity and direction for spontaneous beating by spatial and temporal mapping of calcium peaks. To assess intracellular calcium dynamics, cells are paced from 0.5-5 Hz to evaluate changes in the action potential duration (specifically APD50, interval from time from 50% peak to time 50% baseline, with 4 ROIs/sample, n=3/group).

Drug Responsiveness

Cell sheets and monolayers are treated with 1 μM isoproterenol, β-adrenoreceptor agonist, and 1 μM verapamil, a calcium channel blocker, to observe changes in beating rate (4 ROIs/sample, n=3/group).

Action Potential Profiles

Cardiac tissue sheets are attached to microelectrode arrays to measure action potential profiles across the entire cell sheet. Action potential amplitude, upstroke velocity, and resting membrane potential are determined (in response to chronotropic drugs, described above; n=6).

The results are now described.

Successful intact detachment of cell sheets yield viable (more than 90% live cells), beating cell sheets (at least 80% MHC+) and demonstrate improved contractile and electrophysiological function over isotropic cell sheets and 2D monolayers. Following the preliminary data, cardiac cell sheets from aligned PNIPAAm/PCL fibers have better synchronicity (i.e., less beating variation) than sheets from unaligned fibers. Alignment improves CM function by increasing contraction/relaxation velocity, action potential propagation velocity and persistence, and drug responsiveness. For cell sheet formation, PNIPAAm/PCL fibers generally should consist of primarily PNIPAAm but have a sufficient amount PCL to allow and sustain cell attachment. Consequently, PNIPAAm/PCL fibers with high PCL content may not generate cell sheets of comparable performance.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of making an anisotropic cell sheet, comprising the steps of:
   electrospinning a solution comprising poly(N-isopropylacrylamide (PNIPAAm) and poly(caprolactone) (PCL) having a PNIPAAm to PCL ratio of at least 90% to generate a fiber mat having fibers in substantially parallel alignment;
   culturing cells on the fiber mat in an environment above about 32° C. to form an anisotropic sheet of cells attached to the fiber mat; and
   introducing the fiber mat to an aqueous environment below about 32° C. to release an intact anisotropic sheet of cells.

2. The method of claim 1, wherein the solution comprises 10% to 20% wt/v of the PNIPAAm and PCL mixture dissolved in a mixture of methanol and chloroform.

3. The method of claim 1, wherein the electrospinning is performed using a rotating mandrel.

4. The method of claim 1, wherein the fibers have a PNIPAAm core and a PCL shell.

5. The method of claim 1, wherein the fibers comprise PNIPAAm fibers and PCL fibers.

6. The method of claim 1, wherein the fibers have a diameter between about 1 and 3 μm.

7. The method of claim 1, wherein the fiber mat is wetted with an aqueous solution above about 32° C. prior to the step of culturing cells.

8. The method of claim 1, wherein the fiber mat is pretreated with a cell attachment enhancing composition prior to the step of culturing cells.

9. The method of claim 8, wherein the attachment enhancing composition comprises at least one component selected from the group consisting of: Matrigel, fetal bovine serum, gelatin, chitosan, fibronectin, collagen, poly-l-lysine, and laminin.

10. The method of claim 1, wherein the cells are selected from the group consisting of: urothelial cells, mesenchymal cells, muscle cells, myocytes, fibroblasts, chondrocytes, adipocytes, fibromyoblasts, ectodermal cells, hepotocytes, Islet cells, parenchymal cells, osteoblasts, nerve cells, and stem cells.

11. The method of claim 1, wherein the fiber mat is introduced to an aqueous environment below about 32° C. by immersion or by rinsing.

12. An anisotropic cell sheet formed by the method of claim 1.

* * * * *